(12) United States Patent
Bishop et al.

(10) Patent No.: US 7,951,110 B2
(45) Date of Patent: May 31, 2011

(54) EXPANDABLE SPINAL SHEATH AND METHOD OF USE

(75) Inventors: Joseph Bishop, Menifee, CA (US); Jay Lenker, Laguna Beach, CA (US); Edward J. Nance, Corona, CA (US); Huan T. Nguyen, Santa Ana, CA (US)

(73) Assignee: Onset Medical Corporation, Irvine, CA (US)

( * ) Notice: Subject to any disclaimer, the term of this patent is extended or adjusted under 35 U.S.C. 154(b) by 0 days.

(21) Appl. No.: 12/614,715

(22) Filed: Nov. 9, 2009

(65) Prior Publication Data

US 2010/0145267 A1    Jun. 10, 2010

Related U.S. Application Data

(60) Provisional application No. 61/112,952, filed on Nov. 10, 2008.

(51) Int. Cl.
*A61M 29/00* (2006.01)

(52) U.S. Cl. .............. 604/96.01; 606/191; 606/279; 606/900

(58) Field of Classification Search ......... 604/96.01, 604/103.05, 163, 164.01–164.13; 606/191, 606/279; 623/1.11, 13.15; 600/207
See application file for complete search history.

(56) References Cited

U.S. PATENT DOCUMENTS

| 319,296 A | 6/1885 | Molesworth |
| 4,338,942 A | 7/1982 | Fogarty |
| 4,401,433 A | 8/1983 | Luther |
| 4,636,346 A | 1/1987 | Gold et al. |
| 4,710,181 A | 12/1987 | Fuqua |
| 4,738,666 A | 4/1988 | Fuqua |
| 4,884,573 A | 12/1989 | Wijay et al. |
| 4,898,591 A | 2/1990 | Jang et al. |
| 4,984,564 A | 1/1991 | Yuen |
| 5,057,092 A | 10/1991 | Webster, Jr. |
| 5,059,183 A | 10/1991 | Semrad |
| 5,066,285 A | 11/1991 | Hillstead |
| 5,092,839 A | 3/1992 | Kipperman |
| 5,098,393 A | 3/1992 | Amplatz et al. |
| 5,108,416 A | 4/1992 | Ryan et al. |
| 5,147,316 A | 9/1992 | Castillenti |
| 5,163,903 A | 11/1992 | Crittenden et al. |
| 5,176,659 A | 1/1993 | Mancini |
| 5,250,025 A | 10/1993 | Sosnowski et al. |

(Continued)

FOREIGN PATENT DOCUMENTS

EP        0206553        1/1991

(Continued)

*Primary Examiner* — Nicholas D Lucchesi
*Assistant Examiner* — Gerald Landry, II
(74) *Attorney, Agent, or Firm* — Knobbe, Martens, Olson & Bear, LLP.

(57) ABSTRACT

Disclosed is an expandable percutaneous sheath, for introduction into the body while in a first, low cross-sectional area configuration, and subsequent expansion to a second, enlarged cross-sectional configuration. The sheath is maintained in the first, low cross-sectional configuration by a removable tubular restraint or by structural elements built into the wall of the expandable portion of the sheath. In one application, the sheath is utilized to introduce a formed in place orthopedic fixation rod such as for use in spinal fixation procedures, preparation of a spinal segment, or placement of a vertebral body spacer. The sheath can further comprise structural elements to permit re-collapse of the sheath under fluid pressure following completion of the procedure and prior to removal from the patient.

21 Claims, 14 Drawing Sheets

U.S. PATENT DOCUMENTS

| | | |
|---|---|---|
| 5,256,150 A | 10/1993 | Quiachon et al. |
| 5,279,553 A | 1/1994 | Winkler et al. |
| 5,295,994 A | 3/1994 | Bonutti |
| 5,312,417 A | 5/1994 | Wilk |
| 5,320,611 A | 6/1994 | Bonutti et al. |
| 5,395,349 A | 3/1995 | Quiachon et al. |
| 5,447,503 A | 9/1995 | Miller |
| 5,514,091 A | 5/1996 | Yoon |
| 5,527,336 A | 6/1996 | Rosenbluth |
| 5,573,520 A | 11/1996 | Schwartz |
| 5,657,963 A | 8/1997 | Hinchliffe et al. |
| 5,662,614 A | 9/1997 | Edoga |
| 5,702,373 A | 12/1997 | Samson |
| 5,709,713 A | 1/1998 | Evans et al. |
| 5,766,203 A | 6/1998 | Imran et al. |
| 5,776,141 A | 7/1998 | Klein et al. |
| 5,810,776 A | 9/1998 | Bacich et al. |
| 5,908,435 A | 6/1999 | Samuels |
| 6,030,364 A | 2/2000 | Durgin et al. |
| 6,056,718 A | 5/2000 | Funderburk et al. |
| 6,063,056 A | 5/2000 | Engelberg |
| 6,168,579 B1 | 1/2001 | Tsugita |
| 6,183,443 B1 | 2/2001 | Kratoska et al. |
| 6,187,000 B1 | 2/2001 | Davison et al. |
| 6,197,016 B1 * | 3/2001 | Fourkas et al. ............... 604/537 |
| 6,248,110 B1 * | 6/2001 | Reiley et al. .................... 606/93 |
| 6,248,116 B1 | 6/2001 | Chevillon et al. |
| 6,280,452 B1 | 8/2001 | Mears |
| 6,312,443 B1 | 11/2001 | Stone |
| 6,358,238 B1 | 3/2002 | Sherry |
| 6,443,979 B1 | 9/2002 | Stalker et al. |
| 6,517,551 B1 | 2/2003 | Driskill |
| 6,524,320 B2 | 2/2003 | DiPoto |
| 6,537,247 B2 | 3/2003 | Shannon |
| 6,613,038 B2 | 9/2003 | Bonutti et al. |
| 6,616,678 B2 | 9/2003 | Nishtala et al. |
| 6,638,268 B2 | 10/2003 | Niazi |
| 6,706,017 B1 | 3/2004 | Dulguerov |
| 6,951,555 B1 * | 10/2005 | Suresh et al. ................. 604/524 |
| 6,979,341 B2 * | 12/2005 | Scribner et al. ............... 606/192 |
| 7,033,369 B2 | 4/2006 | Davison et al. |
| 7,135,015 B2 | 11/2006 | Dulak et al. |
| 7,309,334 B2 | 12/2007 | von Hoffmann |
| 7,316,677 B1 | 1/2008 | Dulak et al. |
| 7,329,268 B2 | 2/2008 | Van Nguyen et al. |
| 7,457,661 B2 | 11/2008 | Doty |
| 7,488,337 B2 * | 2/2009 | Saab et al. .................... 606/192 |
| 2001/0012950 A1 | 8/2001 | Nishtala et al. |
| 2001/0037126 A1 | 11/2001 | Stack et al. |
| 2002/0009535 A1 | 1/2002 | Michal et al. |
| 2002/0010440 A1 | 1/2002 | Segesser |
| 2002/0077653 A1 | 6/2002 | Hudson et al. |
| 2002/0099431 A1 | 7/2002 | Armstrong et al. |
| 2002/0161377 A1 | 10/2002 | Rabkin |
| 2003/0065353 A1 | 4/2003 | Horzewski et al. |
| 2003/0195551 A1 | 10/2003 | Davison et al. |
| 2003/0212384 A1 | 11/2003 | Hayden |
| 2003/0216770 A1 | 11/2003 | Persidsky et al. |
| 2004/0006344 A1 | 1/2004 | Nguyen et al. |
| 2004/0236346 A1 | 11/2004 | Parker |
| 2005/0085842 A1 | 4/2005 | Eversull et al. |
| 2005/0124937 A1 | 6/2005 | Kick et al. |
| 2005/0149105 A1 | 7/2005 | Leeflang et al. |
| 2005/0222576 A1 | 10/2005 | Kick et al. |
| 2005/0261692 A1 * | 11/2005 | Carrison et al. ................ 606/79 |
| 2006/0052750 A1 | 3/2006 | Lenker et al. |
| 2006/0084985 A1 * | 4/2006 | Kim ................................ 606/61 |
| 2006/0247602 A1 | 11/2006 | Dulak et al. |
| 2007/0112335 A1 | 5/2007 | Dulak et al. |
| 2009/0177206 A1 * | 7/2009 | Lozier et al. .................... 606/93 |
| 2010/0049003 A1 * | 2/2010 | Levy .............................. 600/199 |
| 2010/0318087 A1 * | 12/2010 | Scribner et al. ................. 606/79 |

FOREIGN PATENT DOCUMENTS

| | | |
|---|---|---|
| WO | WO/99/17665 | 4/1999 |
| WO | WO/03/090834 | 11/2003 |

* cited by examiner

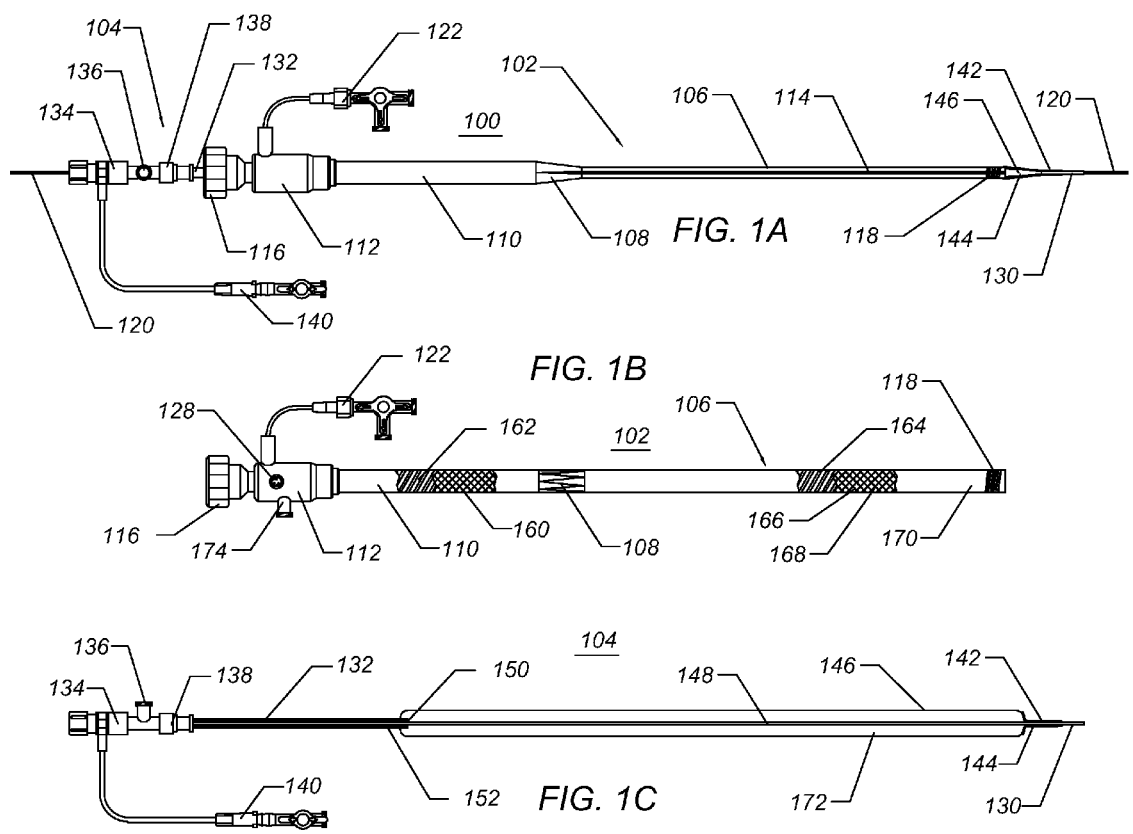

EXPANDABLE SPINAL SHEATH AND METHOD OF USE

PRIORITY CLAIM

This application claims priority to 61/112,952, filed on Nov. 10, 2008, titled Expandable Spinal Sheath and Method of Use, the entirety of which are hereby incorporated herein by reference.

BACKGROUND OF THE INVENTION

1. Field of the Invention

The present invention relates to medical devices and, more particularly, to methods and devices for forming a percutaneous channel. In one embodiment, the present invention relates to a minimally invasive procedure to insert an orthopedic fixation or stabilization implant into the body, such as a formed in situ spinal stabilization rod or performance of a lateral spinal stabilization or reconstruction procedure.

2. Description of the Related Art

The vertebrae and associated connective elements are subject to a variety of diseases and conditions, which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to these diseases, conditions, injuries and manipulations often result from the displacement of all or part of a vertebra from the remainder of the vertebral column. A variety of methods have been developed to restore the displaced vertebrae or portions of displaced vertebrae to their normal position and to fix them within the vertebral column. For example, open reduction with screw fixation is one currently used method. The surgical procedure of attaching two or more parts of a bone with pins, screws, rods and plates requires an incision into the tissue surrounding the bone and the drilling of one or more holes through the bone parts to be joined. Due to the significant variation in bone size, configuration, and load requirements, a wide variety of bone fixation devices have been developed. In general, the current standard of care relies upon a variety of metal wires, screws, rods, plates and clamps to stabilize the bone fragments during the healing or fusing process. These methods, however, are associated with a variety of disadvantages, such as morbidity, high costs, lengthy in-patient hospital stays and the pain associated with open procedures.

Other procedures being practiced today include the Extreme Lateral Innerbody Fusion (XLIF), the Transforamenal Lumbar Innerbody Fusion (TLIF), the Anterior Lumbar Innerbody Fusion (ALIF), and the Posterior Lumbar Innerbody Fusion (PLIF) procedures. The lumbar spine is approached either anteriorly or posteriorly in the ALIF and PLIF procedures, respectively. These are spinal access procedures with different directions of approach. A more recent procedure, the XLIF procedure, allows the spine to be approached from the lateral direction through the Psoras muscle. This type of lateral procedure offer potential benefits in that the spinal cord and major nerve roots are not disposed in the way of the procedure and are less likely to be damaged. Such damage can result in significant patient morbidity. However, the Psoras muscle is highly innervated and damage to these nerves can occur with the procedures, resulting in pain, neuropathy, and numbness. These procedures permit access through a small external incision. The minimally invasive procedures can be performed quickly, with a setup time of 20 minutes after experience is gained.

Therefore, devices and methods are needed for repositioning and fixing displaced vertebrae or portions of displaced vertebrae, which cause less pain and potential complications. Preferably, the devices are implantable through a minimally invasive procedure.

In addition, a wide variety of diagnostic or therapeutic procedures involve the introduction of a device through a natural or artificially created access pathway. A general objective of access systems, which have been developed for this purpose, is to minimize the cross-sectional area of the puncture, while maximizing the available space for the diagnostic or therapeutic instrument. These procedures include, among others, a wide variety of laparoscopic diagnostic and therapeutic interventional procedures. Accordingly, a need remains for access technology, which allows a device to be percutaneously passed through a small diameter tissue tract, while accommodating the introduction of relatively large diameter instruments.

SUMMARY OF THE INVENTIONS

A percutaneous access sheath is provided according to an embodiment of the present invention. The percutaneous access sheath is configured to be inserted in a first, smaller cross-sectional configuration and then be expanded to a second, larger cross-sectional configuration. In one embodiment, subsequent removal of a dilator or obturator can provide a large, substantially constant diameter port access device for the delivery of instrumentation or implants to a target site in the region of the mammalian spine. In another embodiment, the percutaneous access sheath is used to facilitate the insertion of an orthopedic fixation or stabilization implant that is formed in situ, such as a spinal stabilization rod. In other embodiments, the percutaneous access sheath can facilitate placement of preparation of the intervertebral disc and adjacent vertebrae. Following preparation, vertebral body spacers, artificial intervertebral discs, or intervertebral disc implants can be placed through the access sheath.

The percutaneous access sheath can be used in conjunction with a deployment catheter or dilator, which is provided with a balloon at its distal end. In an embodiment, the percutaneous access sheath has a proximal section and a variable diameter distal section. The deployment catheter or dilator can be disposed within the percutaneous access sheath such that the deflated, folded balloon is pre-positioned within the distal section of the percutaneous access sheath.

In an embodiment, the distal section of the percutaneous access sheath can be restrained in a first, small diameter by a releasable restraint such as a perforated insertion sheath. In other embodiments, the distal, expandable section of the sheath can retain its folded configuration without the need of an external jacket. In some embodiments, the distal section of the percutaneous access sheath can be creased along longitudinal folds. These longitudinal folds give the percutaneous access sheath a smaller cross-sectional profile, facilitating its insertion.

In some embodiments, the expandable distal section of the sheath can comprise malleable reinforcing elements. These malleable reinforcing elements can comprise spirals, braids, or complex open metal shapes. The malleable reinforcing elements may be encapsulated within or between outer and inner layers of polymeric surround. In an embodiment, the malleable reinforcing elements are sufficiently strong that they control the force balance between the malleable reinforcing elements and the polymeric surround. In these embodiments, the malleable reinforcing elements are strong enough to resist elastomeric or resilient forces imposed by the polymer. The malleable reinforcing elements are strong enough to resist plastic creep of the polymer. The malleable reinforcing elements are strong enough to resist inwardly directed forces exerted by body tissue that is dilated by the sheath and its dilator. Certain tissues, such as the Psoras muscle, the lumbar muscle, and other muscles of the back or pelvis can exert significant forces on a tubular structure inserted therethrough and these forces can be resisted by the portal or tubular structure. However, in one embodiment, the malleable reinforcing elements are not strong enough to resist remodeling or dilation forces exerted by a sheath dilator disposed inside the expandable distal section and actuated to dilate the expandable distal section, including its malleable reinforcing elements and its polymeric layers. The polymeric layers generally embed the malleable reinforcing elements and prevent translation or slippage between the malleable reinforcing elements and the polymeric surround. An outer sheath is generally not required for these embodiments during the insertion phase of a procedure, but a nose cone can advantageously prevent tissue from becoming entrained or forced into the distal edges of the folded distal expandable section. A packaging support can be provided to maintain a tight wrap and fold configuration for the expandable distal region, following manufacture and during sterilization and storage prior to use.

The percutaneous access sheath may be inserted as described above with the expandable distal section in its first, smaller cross-sectional configuration. To facilitate this, the balloon can be partially inflated, expanding the distal section of the percutaneous access sheath sufficiently to tear the insertion sheath along its perforations. The balloon can be fully inflated to distend the distal section of the percutaneous access sheath to its second, full cross-sectional profile. Afterwards, the balloon can be deflated to allow the removal of the deployment catheter or dilator, leaving the percutaneous access sheath in place. Multiple stages of dilation, otherwise known as serial dilation, can be performed using consecutively larger sheaths to create the entrance pathway.

In one embodiment, where the percutaneous access sheath is used to facilitate the insertion of an orthopedic spinal stabilization implant that is formed in situ, a percutaneous access sheath can advantageously be first inserted through the portals of adjacent bone anchors, by the method described above. This provides a smooth channel to facilitate the passage of another deployment catheter carrying an inflatable orthopedic fixation device at its distal end.

Other aspects of the inventions include methods of use. In some embodiments, the expandable sheath is used to provide a pathway for performance of an XLIF or TLIF procedure on the lumbar spine. In these procedures, the patient is reclined on their right or left side, in a lateral position, depending on the route of access required for the procedure. A small incision is created in the skin. The underlying tissues are explored and the Psoras muscle is located. Care is taken to avoid damaging the lumbar nerves that run through this muscle and run generally just outside the path of a guidewire or sheath. Manipulation of the Psoras muscle is preferably minimized. A guidewire is placed under fluoroscopy, through the skin incision, through the Psoras muscle, and terminating at the intervertebral disc or vertebra being treated. The expandable sheath with its pre-inserted dilator and tapered distal tip, may be inserted, over the guidewire, and routed to the intervertebral disc or vertebra being treated. The sheath may be advantageously advanced until it is proximate, adjacent, or against the vertebral lips. The sheath can be flexible, substantially rigid, or semi-rigid. In some embodiments, flexibility or steering are not as important as the ability to follow the guidewire. The length of the expandable portion of the sheath, in one embodiment, can range between about 8-cm to about 30-cm and preferably between about 10-cm and about 20-cm. The diameter of the inner lumen of the expanded sheath, in one embodiment, can range between about 10-mm and about 25-mm with a preferred range of about 12-mm and about 20-mm (36 French to 60 French). The sheath may then be expanded using a commercial angioplasty balloon dilator, having in one embodiment a capacity of about 20-cc to 40-cc, or more. The sheath can be expanded at balloon pressures ranging from about 10-atmospheres to about 30 atmospheres or more. Following expansion, the dilator may be deflated and removed from the sheath leaving an access portal to the lumbar spine, in this case, or other target region of the spine. Instrumentation can be inserted through the expanded sheath to prepare the site of an implant. This preparation instrumentation is then removed and an implant is placed through the sheath, into the spinal region. The implant can serve as a vertebral disc spacer, inner body fusion device, or motion preserving spinal implant. The implantation delivery systems may then be removed leaving the implant in place. Suitable devices can be used to close any defects in the annulus of the intervertebral disc. The sheath can then be removed and the portal incision closed using standard, accepted procedures. Additional procedures can be performed at other levels of the spine.

In some embodiments, dilation is performed using a multiple stage process. In some embodiments, the sheath is inserted such that the distal end of the dilator is located within the intervertebral disc. In other embodiments, the sheath is inserted such that the distal end of the dilator resides just outside the annulus of the intervertebral disc. Following expansion, secondary instruments are used to dilate or remove the last portion of tissue between the distal end of the sheath and the vertebral lip. In other embodiments, the distal end of the dilator comprises an inverted fold and bond such that the dilator does not extend substantially beyond the distal end of the expandable region of the sheath.

Other applications of the percutaneous access sheath include a variety of diagnostic or therapeutic clinical situations, which require access to the inside of the body, through either an artificially created or natural body lumen.

In some embodiments, the hub of the sheath, as well as the sheath geometry itself can be substantially rectangular or square in cross-section to maximize the ability to pass a rectilinear cross-section implant therethrough.

In an exemplary embodiment, the expandable introducer sheath comprises a proximal, non-expandable section. The proximal section may comprise a composite tubular structure fabricated from an inner polymeric layer of polyethylene, an outer polymeric layer of polyethylene, and a reinforcement layer sandwiched between the two polymer layers. The reinforcement layer can comprise a coil of flat, spring-hardness, stainless steel wire or ribbon with a width of about 0.010 inches, with a range of 0.005 to 0.025 inches, and a thickness of about 0.003 inches, with a range of 0.002 to 0.004 inches. The coil spacing can range between 0.001 inches and 0.050 inches. The proximal, non-expandable region may be affixed at its proximal end to the sheath hub. The distal end of the proximal non-expandable region may be affixed to the proximal end of a transition zone. The distal end of the transition zone can be affixed to a distal expandable region.

The distal expandable region can comprise between 10% and 95% of the catheter shaft length. The distal, expandable region can comprise a reinforcing layer of malleable stainless steel ribbon or flat wire wound into a coil with similar dimensions as in the proximal region. The entire length, or a substantial portion thereof, can comprise an additional reinforcing layer, or layers, of braided material fabricated from materials such as, but not limited to, polyethylene naphthalate (PEN), polyester (PET), stainless steel, titanium, nitinol, cobalt nickel alloy, polyamide, polyimide, or the like. In an embodiment, the reinforcing structure, generally sandwiched between an outer and an inner layer of polymeric wall, can comprise an inner layer of polymer overlaid by a first reinforcing braid layer, overlaid by a coil reinforcement, finally overlaid with an outside layer of polymeric material. In another embodiment, the inner layer of polymeric material is overlaid by the coil reinforcement, which is overlaid by the braided reinforcement, which is finally overlaid with the outside layer of polymeric material. In yet another embodiment, the inner layer of polymeric material is overlaid by the braided layer, which is overlaid by the coil winding, which is overlaid by another layer of braid, which is finally overlaid by the outer polymeric layer.

In an embodiment, the sheath dilator is configured with a PET balloon affixed to a polymeric Hytrel shaft. The Hytrel shaft can comprise an inner and an outer tube concentrically disposed with an annulus open between the two tubes. The distal end of the dilator balloon can be affixed to the inner Hytrel tubing. The proximal end of the dilator balloon may be larger in diameter and can be affixed to the outer Hytrel tubing in this embodiment. The outer Hytrel tubing may extend just inside the center volume of the dilator balloon and the annulus between the outer tube and the inner tube may be in fluid communication, operably connected to, the center volume of the dilator balloon. The annulus may be operably in fluid communication with an inflation port integral to, or affixed to, the dilator hub. In another embodiment, an outer polymer tube, such as the outer Hytrel tube of the preceding embodiment, can be omitted and the dilator balloon can comprise a proximal tail that extends proximally to bond and seal within the dilator hub or sidearm. In this embodiment, the pressurization annulus for the balloon may reside between the dilator balloon and the inner polymer tube, the pressurization annulus being operably connected to an inflation port on the dilator hub. The interior of the inner dilator tube comprises a guidewire lumen, with a diameter of, for example 0.037 to 0.042 inches, suitable for advancing the entire system over a guidewire suitable for percutaneous spinal access. Such guidewires typically are about 0.035 or 0.038 inches in diameter, or larger, and are relatively stiff.

The sheath can be folded into one or more longitudinally oriented folds and wrapped around the dilator, with a collapsed dilator balloon. The malleable elements in the distal expandable regions maintain the configuration of the system in its collapsed state. An optional outer jacket, which can have attached, peel-away, tear-away, or removable before use configurations, can be used to encase part or all of the diametrically collapsed sheath tubing. In other embodiments, the sheath can further comprise a thin FEP, PFA, or polytetrafluoroethylene (PTFE) tube over the outside of the sheath. This fluoropolymer outer covering need not be removed, its function being to protect a soft polyethylene sheath material from hard vascular deposits such as atheroma.

In yet another embodiment, the central region can comprise elastomeric polymer structure with an optional braid reinforcement that permits the central region to simply expand diametrically from a first smaller diameter to a second larger diameter without the use of folds. An internal slip layer of PTFE, FEP, PFA, or other highly lubricious material can be used to facilitate passage of a catheter through the central region to prevent clinging. The internal slip layer can be the inner layer of the polymer sandwich within which the reinforcing coils or braids are embedded.

Once the expandable, spinal introducer sheath system has been advanced so that its distal end reaches proximate, or through, the external aspect of the intervertebral disc, the dilator may be expanded at pressures of between 10 and 40 atmospheres, and preferably between 15 and 30 atmospheres. The dilator may then be deflated and removed from the central lumen of the sheath subassembly.

In other embodiments, the sheath can comprise a flexible shaft configured with an elastomeric outer membrane and a reinforcing layer configured as a braided structure that is capable of changing its diameter. The sheath can be inserted into a patient in a first, smaller cross-sectional configuration, preferably over a small diameter dilator or tapered obturator. The obturator or tapered dilator can then be removed and a hollow central dilator of large diameter may be inserted into the interior lumen of the sheath. Upon insertion of the large diameter, hollow central dilator into the flexible shaft of the sheath, the sheath can expand diametrically to a second, larger, cross-sectional area, diameter, or radius. One or more catheters can be inserted therethrough to reach a target site within the vasculature. Following completion of the procedure, the central dilator can be removed resulting in elastomeric contraction of the outer membrane to a first, smaller cross-sectional area. The sheath can next be removed from the patient in its first, smaller, cross-sectional area configuration. The sheath can be configured using principles and design elements as described in U.S. Pat. No. 7,309,334 by Gerard von Hoffmann, titled "Intracranial Aspiration Catheter", the entirety of which is hereby incorporated herein by reference.

In other embodiments, the sheath can further comprise a pressure jacket surrounding at least a portion of the expandable distal region. The pressure jacket preferably surrounds the entire distal, expandable region. The pressure jacket is advantageously disconnected from the internal sheath tubing except at its proximal and distal ends, where the pressure jacket is securely bonded or welded to the sheath tubing, sheath hub, or both. In an embodiment, the bond between the pressure jacket and the sheath tubing is very secure, reliable, and capable of sealing against fluid pressure even after severe folds or creases have been placed in the bond area by the folding of the distal expandable region of the sheath. The pressure jacket may be operably connected to an inflation port near the proximal end of the sheath by a lumen within the sheath tubing, an annulus, or other fluid-tight fluid-transport structure. The pressure jacket inflation port can comprise a Luer lock or other adapter suitable for attachment to an inflation device such as is used for inflation of an angioplasty balloon, or the sheath being described herein. The inflation device preferably comprises a pressure gauge capable of displaying the pressures being generated thereby. Inflation of the pressure jacket may be accomplished using liquids so that leakage thereof into the cardiovascular system does not generate any gas bubbles or emboli. Pressure generated between the pressure jacket and the sheath tubing can cause the sheath tubing to collapse into a flat, arcuate or other low profile cross-section structure. Pressures necessary to generate sheath re-collapse or re-folding can range from about 1.0 to about 10.0 atmospheres and preferably between about 2.0 to about 6.0 atmospheres. This pressure may be injected into the space between the pressure jacket and the sheath. Following sheath re-collapse or re-folding, a vacuum generated between the sheath pressure jacket and the sheath can collapse the jacket down onto the sheath tubing to facilitate removal from the patient. The pressure jacket can be fabricated from materials such as, but not limited to, PET, polyamide, polyimide, or other high strength material. In an embodiment, the material exhibits substantially no elasticity or expansion beyond its predetermined profile upon application of collapse pressure. The thickness of the pressure jacket can be very small, in the range of about 0.0002 to 0.001 inches to maintain a low profile and because pressure stresses on the structure are relatively low.

The reinforcement of the expandable regions can comprise wire, preferably malleable wire. The wire can have a round cross-section, a rectangular cross-section, a ribbon-like cross-section, or the like. The malleable wire can be bent by a dilator balloon, tapered dilator, hollow dilator, or the like, into the second, larger cross-section and the strength of the malleable wire can substantially overcome any resilient spring-back imparted by the polymeric component of the sheath wall.

In other embodiments, the wire can have elastomeric properties or shape memory properties. These embodiments can utilize shape-memory wire, pseudoelastic wire, superelastic wire, elastomeric wire, or the like. The wire can be nitinol, stainless steel, cobalt nickel alloy, or the like. The wire, in its shape-memory configuration can have an austenite finish temperature of around 25 to 35 degrees centigrade, preferably between 28 and 32 degrees centigrade so that body temperature blood causes the wire mesh to be biased to its larger, expanded configuration.

In another embodiment, the expandable region can comprise polymeric encapsulation of a braided or otherwise expandable shape memory reinforcing structure. The reinforcing elements or structure can have shape-memory characteristics. The sheath may be inserted into the patient in its first, small cross-sectional area. The reinforcing elements may be maintained below the martensite start temperature so that the reinforcing elements are substantially malleable, even at body temperature (approximately 37° C.). The sheath wall can then be dilated with the balloon dilator as described herein. The dilator may then be removed and the sheath becomes host to therapeutic or diagnostic catheters, which are inserted therethrough. Following removal of the catheters, electricity can be applied to lead wires at the proximal end of the sheath. The electrical leads are operably connected to heaters in the vicinity of the reinforcing elements, or the electrical leads are operably connected to each end of the reinforcing elements. The electricity causes Ohmic, or resistive, heating of the reinforcing elements to above their austenite finish temperature. The reinforcing structure, having been shape-set in its small diameter configuration, returns to that small diameter configuration, bringing the entire expandable sheath wall down with it, to facilitate removal of the sheath from the patient. An austenite finish (Af) temperature of around 42° C., or higher, can be used in this application.

The dilator catheter tubing can comprise an inner and outer member. The materials of the inner member and the outer member can comprise Hytrel, Pebax, polyether ether ketone (PEEK), composite, reinforced construction, polyester, polyurethane, polyethylene, or the like. The catheter hub can be fabricated from materials such as, but not limited to, polycarbonate, acrylonitrile butadiene styrene (ABS), polyurethane, polyvinyl chloride, and the like. The dilator balloon can be fabricated from stretch blow-molded polyester polyamide, polyamide, or polyester blends, using materials such as, for example, Eastman PET 9921 or similar.

In another embodiment, a coating can be applied to the expandable areas to generate an inwardly biased, radially oriented contraction force on the sheath. The expandable area can be forced to expand radially against the bias force of the coating. Once the radial expansion force is removed, the expandable area may remain biased radially inward toward its smallest diameter, to which it will travel unless prevented from doing so. An internal dilator can be advanced axially, in the distal direction, into the lumen defined within the expandable distal region of the sheath. The internal dilator can maintain the sheath open lumen until removed proximally, at which point the sheath distal expandable tubing can contract in diameter back to a smaller size. This reduction in sheath diameter can be beneficial if performed prior to sheath removal since it reduces shear force on the myocardium during sheath removal and can improve the healing response of the tissue.

The system can comprise radiopacity enhancements to improve visualization under fluoroscopy. Radiopaque (RO) markers can be affixed to the distal end of the sheath to denote its distal end, the extents of the expandable region or regions, or even the orientation of the sheath by mounting the RO markers asymmetrically on the tubing. The radiopaque markers can comprise bands or windings of metal such as, but not limited to, tantalum, platinum, platinum iridium, gold, and the like.

In certain embodiments of the sheath wall construction, an inner layer of polymer and an outer layer of polymer sandwich a reinforcing layer. The reinforcing layer can be a coil of metal such as, but not limited to, titanium, stainless steel, cobalt nickel alloy, nitinol, tantalum, and the like. In the distal, expandable region, the coil is preferably malleable, with little or no spring properties, and does not exhibit any elastomeric tendencies. The coil can be fabricated from flat wire with a thickness of about 0.001 to 0.010 inches and preferably about 0.002 to 0.005 inches. The width of the flat wire can range from about 0.005 to 0.050 inches and preferably from about 0.008 to 0.025 inches. The spacing between the coils can, for example range from substantially 0 to approximately 5 times the width of the coil wire. The coil spacing may be non-zero to permit bonding of the outer layer and the inner layer of polymer surround on the sheath, thus a coil spacing of about 0.5 to 3 times the coil width is preferred. The coils can be fabricated from round stock, flat stock, or the like. The reinforcement can be sandwiched between the inner layer and the outer layer of polymeric material, wherein the inner and outer layers can be bonded or welded to each other through the space between the coils. The inner and outer polymeric layers can be fabricated from the same or different materials. Suitable materials for the inner and outer layers include, but are not limited to, polyurethane, silicone, Hytrel, Pebax, PEEK, polyethylene (PE), high density polyethylene (HDPE), low density polyethylene (LDPE), polyester, polyethylene blends, and the like. In yet another embodiment, a plastically deformable, malleable, or annealed, braid structure can also be used for reinforcement to beneficially eliminate the need for the malleable coil and permit a reduction in wall thickness while retaining the tensile strength and torqueability of the braid.

In some embodiments, the sheath retains substantially constant flexibility moving from the proximal to the distal end. The distal, expandable region, in its first, smaller cross-sectional configuration, is generally more flexible than the fully expanded proximal region of the sheath, but the distal end can be made more rigid by use of a guidewire and stiff materials such as metals in the dilator shaft. In certain embodiments, the sheath shaft can comprise multiple regions of varying flexibility along the axial length of the shaft. In some embodiments, the catheter shaft can have at least two regions of different flexibility. In other embodiments, the catheter shaft can comprise three regions of different flexibility. In yet other embodiments, the sheath shaft flexibility can be reduced toward the proximal end of the catheter and increased moving toward the distal end of the catheter. Moving from the proximal to the distal end of the catheter shaft, the flexibility of a given discreet section can be greater than the flexibility of the region just proximal and adjacent to said discreet section. A sheath having a substantially collapsed, small diameter distal region can exhibit significantly increased flexibility in that area over its flexibility in non-expandable, or fully expanded, expandable regions. Following such traverse, the sheath can be expanded to create a stiffer, larger diameter structure.

For purposes of summarizing the inventions, certain aspects, advantages and novel features of the inventions are described herein. It is to be understood that not necessarily all such advantages may be achieved in accordance with any particular embodiment of the inventions. Thus, for example, those skilled in the art will recognize that the inventions may be embodied or carried out in a manner that achieves one advantage or group of advantages as taught herein without necessarily achieving other advantages as may be taught or suggested herein. These and other objects and advantages of the present inventions will be more apparent from the following description taken in conjunction with the accompanying drawings.

BRIEF DESCRIPTION OF THE DRAWINGS

A general architecture that implements the various features of the inventions will now be described with reference to the drawings. The drawings and the associated descriptions are provided to illustrate embodiments of the inventions and not to limit the scope of the inventions. Throughout the drawings, reference numbers are re-used to indicate correspondence between referenced elements.

FIG. 1A is a side elevational view of a percutaneous, spinal access sheath with its distal expandable region in its first, smaller cross-sectional configuration, according to an embodiment of the invention;

FIG. 1B is a side elevational view of the percutaneous, spinal access sheath of FIG. 1A with its distal expandable region in its second, larger cross-sectional configuration, according to one embodiment;

FIG. 1C illustrates the expanded percutaneous spinal access sheath dilator separated from the sheath, in side view, according to one embodiment;

DETAILED DESCRIPTION OF THE PREFERRED EMBODIMENTS

Figure 2A:
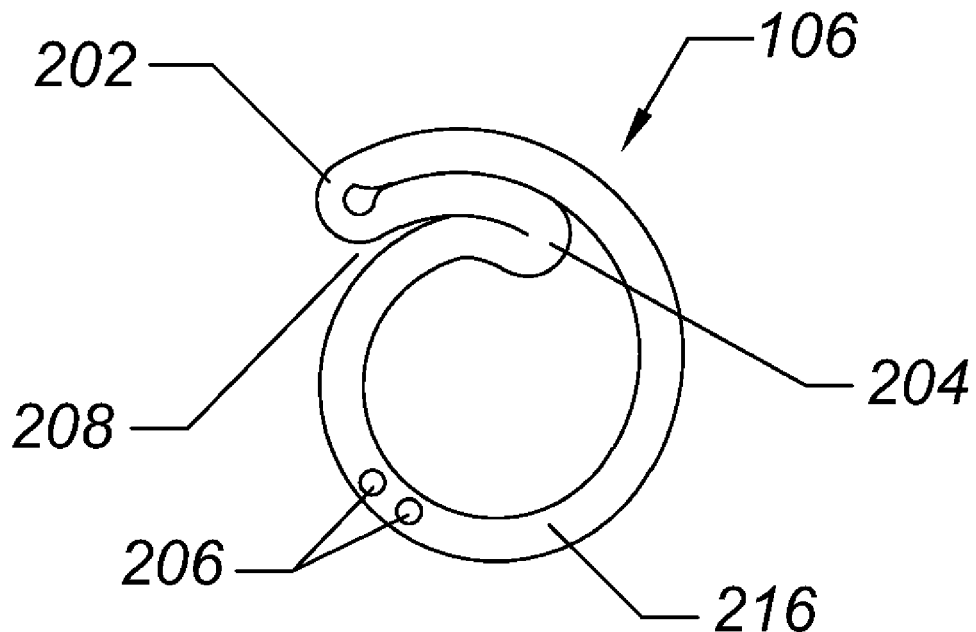
FIG. 2A illustrates a lateral cross-section of the distal expandable section of a sheath comprising a single fold, according to one embodiment.

The inventions may be embodied in other specific forms without departing from its spirit or essential characteristics. The described embodiments are to be considered in all respects only as illustrative and not restrictive. The scope of the inventions are therefore indicated by the appended claims rather than the foregoing description. All changes that come within the meaning and range of equivalency of the claims are to be embraced within their scope.

As used herein, a catheter or sheath can be described as an axially elongate structure having a proximal end, a distal end, and a lumen extending partially, or completely, therethrough. As used herein, the terms proximal and distal refer to directions or positions along a longitudinal axis of a catheter or medical instrument. Proximal refers to the end of the catheter or medical instrument closest to the operator, while distal refers to the end of the catheter or medical instrument closest to the patient. For example, a first point is proximal to a second point if it is closer to the operator end of the catheter or medical instrument than the second point. However, the terms anatomically proximal and anatomically distal refer to orientations within the body. For example, a point is more anatomically distal if it is further from the heart than a point described as anatomically proximal.

FIG. 1A is a side view of one embodiment of a percutaneous, spinal access sheath system 100 with its distal expandable region in its first, smaller cross-sectional configuration. The sheath system 100 may comprise a sheath 102 and a dilator 104. The sheath 102 may comprise a non-expandable proximal region 110, a transition zone 108, an expandable distal region 106 further comprising a fold 114 and one or more expandable radiopaque markers 118, a sheath hub 112 further comprising an optional sealing valve 116, and a purge port 122. The dilator 104 may further comprise a dilator hub 138, a length of proximal tubing 132, a sealing valve 134, a dilator inflation port 136, a length of central tubing 130 further comprising a guidewire lumen 148, a dilatation balloon 146, an optional distal fairing 144, and a distal balloon bond 142. A guidewire 120 is shown disposed through the central lumen of the dilator 104.

Referring to FIG. 1A, the sheath hub 112 can be coupled to the proximal end of the non-expandable tubing region 110. The distal end of the non-expandable tubing region 110 can be coupled to the proximal end of the distal expandable region 106 by the transition zone 108. The dilator 104 can be slidably disposed within the lumen of the sheath 102 and held in place axially by compression of a lock or sheath valve 116 against the hub 138 or tubing 132 of the dilator 104. The dilator 104 can be further held in place by collapse and radial compression of the expandable distal region 106. The dilator balloon 146 can be bonded, welded, or otherwise affixed to the dilator catheter tubing 130 and 132 by the bond 142 at the distal end of the dilator balloon 146. The dilator balloon 146 can be fully deflated and wrapped around the dilator inner catheter tubing 130 prior to insertion inside the sheath 102. The dilator hub 138 can be coupled or affixed to the proximal end of the dilator catheter tubing 132. The dilator inflation port 136 can be affixed, coupled, or integral, to the dilator hub 138 and can be operably connected to a balloon inflation lumen (not shown) within the hub 138 and within the dilator tubing 130 or 132, or an annulus 150 (see FIG. 10) between the two dilator tubes 130 and 132. The sheath radiopaque marker 118 can be coupled to, or embedded within, the folded distal section 106.

The sheath purge port 122 can be coupled, affixed, bonded, or insert molded to the sheath hub 112 and can comprise a flexible length of axially elongate tubing with a central lumen. The sheath purge port 122 is preferably terminated with a Luer lock fitting, a stopcock, or other type of valve. The sheath purge port 122 can be operably connected to the interior lumen of the sheath 102 and is suitable for purging of air or aspiration of fluids therethrough. The dilator purge port 140 can be affixed, integral to, or coupled to the dilator hub 138 and is operably connected to the central guidewire lumen (not shown) of the dilator 104. The dilator purge port 140 may be terminated with a Luer lock fitting or a stopcock or other type of valve. The dilator purge port 140 can be operably connected to the interior lumen of the sheath 102 and is suitable for purging of air or aspiration of fluids therethrough.

The sheath hub 112 can comprise ports that further comprise, or are terminated by, valves 116. The valve 116 is configured to prevent hemorrhage from, or air intake into, the lumen of the sheath subassembly 102. The valve 116 can comprise between one and 5 elements to form a seal against nothing inserted into the valve, form a seal against a maximum diameter object inserted through the valve, and form a seal against anything of intermediate size inserted through the valve. The valve elements 116 can be fabricated from soft silicone or other elastomer. The valve elements 116 can be coated or impregnated with lubricious coatings such as silicone oil or hydrophilic layer. The valve elements can comprise duckbill valves, pinhole valves, slit valves, X-slit valves, ring seals, and the like. The sheath hub 112, and any other housings associated therewith, can be fabricated from relatively rigid polymers such as, but not limited to, acrylonitrile butadiene styrene (ABS), polyurethane, PVC, PET, polycarbonate, polysulfone, and the like.

In FIG. 1A, the distal expandable region 106 and the transition zone 108 are illustrated in their first, smaller cross-sectional configuration. The transition zone 108 may form a taper between the diametrically collapsed expandable region 106 and the larger proximal non-expandable tube or region 110. One sheath radiopaque marker 118, which can number between 1 and 5, is shown located near the distal end of the expandable, distal region 106. The sheath radiopaque marker 118 can be fabricated from gold, platinum, or tantalum wire and can be wound and embedded within the wall of the distal region 106. Radiopaque wire diameters ranging from 0.001 to 0.005 inches in diameter can be used for this application and approximately 3 to 10 winds or turns, with a preferred number of 4 to 6 winds offer suitable visibility under fluoroscopy. The wires have the benefit of being able to be folded or creased along with the rest of the distal expandable region so the radiopaque marker 118 can collapse with the rest of the distal expandable region 106.

The distal sheath tubing 106 can be folded longitudinally 114 in a predetermined pattern comprising between one and four exterior fold edges, wherein the folds extend all the way from about the proximal end of the transition zone 108 to the distal end of the distal sheath tube 106. In the illustrated embodiment, the distal portion 106 comprises a longitudinal fold 114 running parallel to the longitudinal axis of the distal portion 106. The fold 114 can comprise two outer edges and two internal edges. The fold 114 extends from the distal end of the distal portion 106 to the proximal end of the distal portion 106 and extends across a substantial portion of the transition zone 108 to a point where it dissipates near the proximal end of the transition zone 108.

The distal end of the distal portion 106 can be covered with the proximal end of the distal fairing 144. The distal fairing 144 can be configured to cover the distal exposed edge of the distal sheath tube 106 to provide a smooth taper against which the sheath system 100 can be advanced into the side, abdomen, or back of the patient. The distal fairing 144 can be elastomeric and can be stretched slightly over the distal end of the distal portion 106. The distal fairing 144 can be coupled to the inner dilator tube 130 by bonding, welding, or the like. The distal fairing 144 can be fabricated from elastomeric materials such as, but not limited to, Hytrel, Pebax, silicone, thermoplastic elastomer, polyurethane, or the like. The distal fairing 144 can further comprise barium sulfate or bismuth sulfate in concentrations between 5% and 40% to improve radiopacity. The guidewire 120 is a separate device over which the sheath 100 rides, but is illustrated inserted through the central lumen 148 of the dilator 104.

FIG. 1B illustrates an embodiment of the spinal sheath subassembly 102 following expansion of the balloon 146 on the dilator 104, re-collapse of the dilator balloon 146, and subsequent removal of the entire dilator 104 (FIG. 1A). The sheath subassembly 102 is illustrated in partial breakaway view. The sheath subassembly 102 is illustrated in its second, fully expanded, larger configuration. Expansion has occurred in the distal expandable region 106 and in the transition zone 108. Expansion, as defined herein, describes dimension changes in a direction lateral to the longitudinal axis of the sheath subassembly 102. The sheath subassembly 102 may comprise the distal portion 106, the transition zone 108, the proximal portion 110, the sheath hub 112, the optional sheath main valve 116, and the sheath purge port 122. The proximal portion 110 may further comprise a braid reinforcement 160 and an optional coil reinforcement 162. The distal portion 106 may further comprise a malleable coil reinforcement 164, one or more radiopaque markers 118, an optional stabilization balloon 152, an inner polymer layer 168, an outer polymer layer 170, and an optional braid reinforcement 160. The transition zone 108 can comprise reinforcement elements from the proximal region 110, the distal region 106, or both. The transition zone 108 can blend the properties of the proximal region 110 and the distal region 106. The properties of the two regions 110 and 106 can be interdigitated within the transition zone 108 such that tapered fingers describe the boundary therebetween. The sheath hub 112 may further comprise the optional stabilization balloon inflation port 174 and the optional electrical input connector 128 for resistive heating of shape memory reinforcing structures such as 164, 166, or both.

Referring to FIG. 1B, in an embodiment, malleable reinforcing structures within the transition zone 108 and the distal expandable region can maintain the sheath 102 in its second, larger, cross-sectional configuration. The reinforcing elements can comprise structures such as, but not limited to, spiral windings of flat or round wire, braided elements of polymeric strands, wire, a mesh structure similar to a stent, a slotted tube with overlapping longitudinally oriented slots, or the like. In an alternative embodiment, the distal expandable region 106 can comprise reinforcing elements 164, 166 similar to those used in the proximal expandable region 110. The polymers used in the distal expandable region can include materials such as, but not limited to, polyethylene, HDPE, LDPE, polyethylene blends, Hytrel, Pebax, PFA, FEP, PTFE, and the like. Malleable materials such as the polyethylene materials may plastically deform under force of the dilator balloon 146 and offer the benefit of remodeling from a small diameter flexible structure to a large diameter, relatively inflexible structure capable of guiding catheters therethrough. In yet other embodiments, the distal expandable region 106 can comprise shape-memory reinforcing elements 164, 166, or both, that can be heated or cooled to generate austenite or martensite conditions, respectively, that further can be used to drive the sheath wall from one cross-sectional configuration to another. The radiopaque marker 118 can be malleably expanded to conform to the sheath cross-sectional shape in the distal expandable region 106.

In practice, an inner sheath layer 168 may first be laid down over a PTFE-coated stainless steel mandrel (not shown). The sheath inner layer 168 is preferably fabricated from lubricious materials such as, but not limited to, polyethylene, HDPE, LDPE, blends of HDPE and LDPE, PTFE, FEP, PFA, Hytrel, Pebax, or the like. The sheath inner layer 168 can also be coated, on its inner surface, with friction retarding materials such as, but not limited to, silicone oil, polyurethane-based hydrophilic slip coating materials, and the like. The mesh layers 160 and 166 may next be applied over the inner layer 168. The coil reinforcement layers 162 and 164 may then be applied over the mesh reinforcement layers 160, 166. In other embodiments, a second layer of mesh can optionally be applied over the coil layers 162, 164. The second layer of mesh can have different properties from the inner layer, including different filament diameter, filament count, number of picks, and filament density or angle. Finally, an outer layer of polymeric material 170 may be applied over the reinforcement, after which shrink tubing may be placed around the entire structure and heated to shrink, melt, fuse, and bond the inner layer 168 to the outer layer 170 while sandwiching the reinforcing layers therebetween. The outer layer 170 may melt and bond to the inner layer 168 through the spaces between the coil layers 162, 164 and the mesh layers 160, 166. The sheath inner layer 168 can have a wall thickness ranging between about 0.0005 and 0.010 inches with a preferred range of about 0.001 and 0.006 inches. The sheath outer layer 170 can have a wall thickness ranging between about 0.001 and 0.010 inches with a preferred range of about 0.002 to 0.006 inches.

The mesh 160, 166 can be formed from a braid, weave, knit or other structure formed into a tubular cross-section. The mesh 160, 166 can be fabricated from flat or round strands. The mesh 160, 166 can be fabricated from polymers such as, but not limited to, polyethylene naphthalate (PEN), PET, polyamide, polyimide, or the like. The mesh 160, 166 can also be fabricated from metals such as, but not limited to, malleable stainless steel, spring stainless steel, nitinol, titanium, cobalt nickel alloy, tantalum, gold, platinum, platinum alloy, and the like. The lateral size of the strands of the mesh 160, 166 can range between 0.001 and 0.010 inches in at least one dimension. The number of ends of the mesh 160, 166 can range between 2 and 50. The mesh 160, 166 can comprise a pick count of between about 10 and 100 per inch with a preferred range of about 20 to 80 picks per inch.

The construction of the distal sheath tube 106 can comprise a coil of wire 164 with a wire diameter of 0.001 to 0.040 inches in diameter and preferably between 0.002 and 0.010 inches in diameter. The coil 164 can also comprise a ribbon wire or a flat wire that is 0.001 to 0.010 inches in one dimension and 0.004 to 0.040 inches in the other dimension. Preferably, the flat wire is 0.001 to 0.005 inches in the small dimension, generally oriented in the radial direction of the coil, and 0.005 to 0.020 inches in width, oriented perpendicular to the radial direction of the coil. The pitch of the coil 164, which is related to the spacing between coil turns can range from about 0 to about 5 times the ribbon width or wire diameter. Preferably, some space exists between the coil turns to permit bonding between the outer layer 170 and the inner layer 168, so a preferred spacing is between 0.5 and 4 times the width of the ribbon. The outer layer 170 of polymeric material can have a wall thickness of 0.001 to 0.020 inches and the inner layer 168 can have a wall thickness of between 0.001 and 0.010 inches. The wire used to fabricate the coil 164 can be fabricated from annealed materials such as, but not limited to, gold, stainless steel, titanium, tantalum, nickel-titanium alloy, cobalt nickel alloy, and the like. The wire is preferably fully annealed and maintains a malleable state. The wires can also comprise polymers or non-metallic materials such as, but not limited to, PET, PEN, polyamide, polycarbonate, glass-filled polycarbonate, carbon fibers, or the like. The wires of the coil reinforcement 164 can be advantageously coated with materials that have increased radiopacity to allow for improved visibility under fluoroscopy or X-ray visualization. The radiopaque coatings for the coil reinforcement can comprise gold, platinum, tantalum, platinum-iridium, and the like. The mechanical properties of the coil 164 may be such that it is able to control the configuration of the fused inner layer 168 and the outer layer 170. When the distal region 106 is folded to form a small diameter, the polymeric layers 168, 170, which can have some memory, may not generate significant or substantial springback. The sheath wall is preferably thin so that any forces it imparts to the tubular structure are exceeded by those forces exerted by the malleable distal reinforcing layers 164, 166. Additionally, a peel away, slide away, or otherwise removable protective sleeve (not shown) is optionally useful but not necessary to maintain the collapsed sheath configuration. A storage splint (not shown) can be used to maintain the sheath in its collapsed condition during storage and shipping. The storage splint can be removed by the operator, prior to use.

The entire sheath subassembly 102, which comprises a central lumen (not shown), may comprise an approximately constant inner diameter along its entire length. The approximately constant diameter is beneficial in that objects of large diameter, such as prosthetic heart valves, can be inserted and advanced completely from the proximal end and out the distal end of the sheath subassembly 102. The sheath subassembly 102 is illustrated in partial breakaway view to show the coil reinforcement layers 162 and 164 along with the mesh 160 and 166. The optional electrical input connector 128 may be affixed to, and operably connected to, an electrical bus 206 (FIG. 2A) running within the wall of the proximal portion 110, the transition zone 108, and the distal region 106 as well as within the sheath hub 112. The distal end of the electrical bus 206 (FIG. 2A) may be affixed to, and operably connected to, either one or both reinforcement layers 164 or 166. The stabilizer balloon input port 174 may be terminated with a Luer lock female fitting and is operably connected to a balloon inflation lumen 208 (FIG. 2B) within the wall of the proximal portion 110, the transition zone 108, and the distal portion 106, as well as within the hub 112. The balloon inflation lumen 208 may be small and can extend as a bump, in cross-section, that extends outside the normal outside diameter of the sheath walls.

FIG. 19C illustrates the dilator 104 following removal from the lumen of one embodiment of the sheath subassembly 102. The dilator balloon 146 is illustrated in its expanded configuration for the purpose of clarity. The dilator 104 may comprise the outer dilator shaft 132 further comprising the outer dilator shaft lumen 150, the inner dilator shaft 130 further comprising a guidewire lumen 148, the dilator balloon 146 further comprising an internal volume 172, the proximal and distal balloon bonds 152, 142 respectively, the dilator hub 138, the dilator inflation port 136, the dilator valve 134, and the dilator purge port 140.

Referring to FIG. 19C, the dilator balloon 146 can be an angioplasty-type balloon, fabricated from materials such as, but not limited to, PET, PETG, polyamide, polyamide, copolymers of the aforementioned, reinforced polymers, or the like, with wall thickness ranging between about 0.0005 to 0.006 inches with a preferred range of about 0.0008 to 0.003 inches, and capable of containing an internal pressure of 10 to 30 atmospheres, or higher. The dilator balloon 146 may be filled with incompressible fluid such as, but not limited to, saline, radiographic contrast media, Ringer's lactate, or the like by the operator, through a balloon inflation port 804, integral, or affixed, to the dilator hub 138.

The dilator balloon 146 may comprise diametric neck down regions, or bonds 142 and 152, at its distal and proximal ends, respectively. The dilator balloon 146 may be affixed to the outer dilator shaft 132 or the dilator hub 138 at the proximal neck down region 152. The dilator balloon 146 can be affixed to the sheath inner tubing 130 at the distal neck down region 142 using adhesives, welding, or a combination thereof. The dilator balloon 146 may comprise a flat length at least as long as the combined length of the sheath expandable distal region 106 and the transition zone 108, and is preferably somewhat longer to facilitate manufacturability and reliability. The dilator balloon 146 can comprise an inflated diameter approximately equal to or slightly greater than that of the fully expanded distal region 106 of the sheath. Note that the distal fairing 144, which may be beneficially fabricated from soft elastomeric materials, may expand and fold distally off the shoulders of the balloon 146 such that when the balloon 146 is deflated, the fairing 144 returns to a small diameter that can be withdrawn proximally through the lumen of the sheath subassembly 102.

In some embodiments, a long proximal neck down region is provided on the balloon 146. In these embodiments, fluid pressure applied to the inflation port 136 on the dilator hub 138 is operably connected to the annulus between the dilator balloon 146 and the inner catheter shaft 130, allowing balloon inflation fluid such as radiopaque dye contrast media, saline, or the like to be routed into the balloon internal structure and causing the balloon to forcibly expand diametrically. This arrangement can result in a beneficial increase in rated balloon burst, or inflation, pressure. Rated balloon burst pressures in excess of about 25 to 30 atmospheres can be achieved with 99.9% reliability and 95% confidence. In yet other embodiments, the fluid pressure is applied to the balloon through the annulus 150 within the dilator outer tubing 132 not occupied by the inner tubing 130.

In other embodiments, the expandable region 106 can comprise shape memory reinforcing elements 164 or 166, or both, fabricated from nitinol, which is configured with an austenite finish temperature, and preferably the austenite start temperature, in excess of body temperature (normally around 37 degrees centigrade). The sheath system 100 can be inserted into the heart. In its first, martensitic configuration, the reinforcing elements 164 or 166 can be expanded malleably using the dilator 104 as shown in FIG. 19C. At the end of the procedure, the expandable region 106 can be heated by application of electricity to generate resistive heating, causing a temperature increase to above the austenite finish temperature. A suitable austenite finish temperature can range from 38 to 50 degrees centigrade. Such heating can be performed at the conclusion of the procedure, following removal of any therapeutic or diagnostic instruments from the center of the sheath. The shape memory elements can be heat set to a collapsed, small diameter configuration to which they will be biased following application of resistive heating. The reinforcing structures can be configured as a braid, a spiral winding, a woven mesh, a slotted tube, or the like. For the purpose of manufacturing, the reinforcing structures can be heat set in a collapsed, or small diameter, configuration and then be cooled to below martensite finish temperature, at which point the reinforcing structures can be expanded for coating with a polymer or other suitable manufacturing process.

In the re-collapsible embodiments, the expandable region 106 can be re-collapsed to its third, smaller cross-sectional configuration by application of heat to the shape-memory reinforcement embedded within the expandable region. The expandable region 106 can be made to uniformly compress to a smaller diameter, or it can be made to fold into any of a variety of cross-sectional patterns exhibited by a tube that is folded along longitudinally disposed folds. In the embodiments where uniform reduction in cross-sectional shape is imparted, the reinforcement can comprise a braid that elongates longitudinally when it reduces its diameter. The polymeric surround of the expandable region 106 is preferably elastomeric and comprises materials such as, but not limited to, polyurethane, thermoplastic elastomer, silicone elastomer, and the like. The interior of the wall of the expandable region is advantageously coated with a layer of high lubricity and low friction to facilitate catheter or device introduction therethrough without hang-up. Such low friction structures include fluoropolymers such as, but not limited to, PTFE, PFA, FEP, and the like. The interior can also be coated with silicone oil, hydrophilic layers such as those fabricated using polyurethane, and the like.

In another embodiment, the expandable region 106 can be maintained with an open inner lumen if a hollow sleeve or dilator (not shown) is inserted therethrough, or if the expandable region 106 has at least some hoop strength gained by appropriate wall design or reinforcement within the wall. The hollow sleeve or dilator (not shown) can comprise a hollow axially elongate tube with a proximal end and a distal end. The tube can comprise structures and materials that impart flexibility to the hollow sleeve or dilator but the tube advantageously comprises the properties of column strength and kink-resistance. The proximal end of the tube comprising the hollow sleeve or dilator can be affixed to a sleeve hub. The structure of the tube comprised by the hollow sleeve or dilator is preferably very thin and can further comprise a single material, preferably polymeric, or it can comprise a built-up, composite structure with a reinforcing layer and a polymeric surround. The reinforcing layer can comprise a braid, weave, helical coil, slotted tube, or the like. In an embodiment, the hollow sleeve or dilator tube can comprise polymeric surround materials such as, but not limited to, polyamide, polyamide, polyurethane, polyester, polyether ether ketone, Hytrel, or the like. The length of the hollow sleeve or dilator tube may be sufficient to extend from the proximal end of the sheath hub 112 to the distal end of the expandable region 106 while the hollow sleeve hub extends out the proximal end of the sheath 100. The distal end of the hollow sleeve or dilator tube can comprise a bevel on its outer surface to assist with coercing the sheath expandable region 106 to expand from its first, smaller cross-sectional area to its second, larger cross-sectional area. The distal end of the hollow sleeve or dilator tube can further comprise shape-memory elements that are bent radially inward at the distal end in their Martensitic phase and then, upon exposure to body temperature blood, they expand radially outward to form a straight, non-inwardly beveled distal end. In yet another embodiment, an obturator is provided which closely fits the inside diameter of the hollow sleeve or dilator tube and which comprises a tapered distal end suitable for advancement into a body lumen, vessel, or expandable sheath tube. The hollow sleeve or dilator tube may be advanced into the expandable sheath as a unit. The obturator can comprise a hub at its proximal end that releasably snaps or connects to the distal end of the hollow sleeve or dilator tube hub. Once the composite structure is advanced completely into the expandable sheath, the obturator can be removed revealing the large central lumen suitable for the introduction of catheters, instruments, implants, and the like.

The dilator 104 may be slidably disposed within the central lumen of the sheath subassembly 102 and may further comprise an expandable dilator 146 such as, but not limited to, an angioplasty type balloon (as illustrated), a malecot, a reverse collet, or other device capable of expansion to approximately 0.2-mm (0.5 French), or greater, larger than the diameter of the sheath. The balloon 146 can be inflated through the inflation lumen within the catheter shaft 150, which is operably connected, at its proximal end, to a dilator hub 138 or inflation port 136. Following inflation, which expands the distal end 106 of the sheath 102, the dilator expansion element, such as the balloon 146, can be deflated or collapsed, following which it can be removed from the sheath subassembly 102 along with the distal fairing or nose cone 144.

In other embodiments, the exterior of the sheath, and optionally the internal lumen of the sheath, can be coated with a lubricious coating comprising materials such as, but not limited to, silicone oil or a hydrophilic hydrogel comprising polyethylene glycol, polyether polyurethane, or the like. Other coatings can include antimicrobial coatings such as those fabricated from silver azide or anticoagulant coatings such as those comprising heparin.

The length of the sheath system 100 may be sized such that the distance between the transition zone 108 and the distal end radiopaque marker 118 ranges between 10 and 30-cm with a preferred range of between 15 and 25-cm. The diameter of the expanded distal region 106, which may approximate that of the proximal region 110, can range between 10 and 40-mm with a preferred range of between 15 and 35 mm. In this embodiment, the distal section 106 is creased, folded inwards, and collapsed from a larger to a smaller cross-sectional profile to ease its insertion. As discussed below, in one application of the invention, the distal section 106 may be inserted through adjacent bone screws or anchors. Its length can thus be determined by the distance between such adjacent bone screws, and is generally in the range of 4-12 cm. The proximal end 110 of the tubing 102 can be flared and fitted onto a handle 112. A distal cap (not shown) can be threaded onto the handle 112 or hub to secure the proximal end 110 of the tubing 110. Additionally a proximal cap (not shown) can be threaded onto the handle 112. The overall length of the tubing 110 can depend on the distance between the insertion and treatment locations, and is generally in the range of 15-60 cm for orthopedic fixation surgery of the vertebrae. In the illustrated embodiment the length of the tubing is approximately 20 cm, with the distal section 106 accounting for approximately half of that length.

FIG. 2A illustrates a lateral cross-sectional view of one embodiment of a folded distal section 106 comprising a distal section wall 216. The distal section wall 216 may comprise a single fold 208 further comprising a single outside edge 202 and a single inside edge 204. With a small diameter distal section 106 and a relatively thick wall 216, a single fold is the easiest structure to create during manufacturing. The sheath wall 216 further comprises an optional electrical bus 206 fabricated from stainless steel, silver, copper, or other conductor metal for use in transmitting electrical energy from the sheath hub to distal regions of the sheath. The electrical bus can traverse the entire length of the sheath tubing in some embodiments.

Figure 2B:
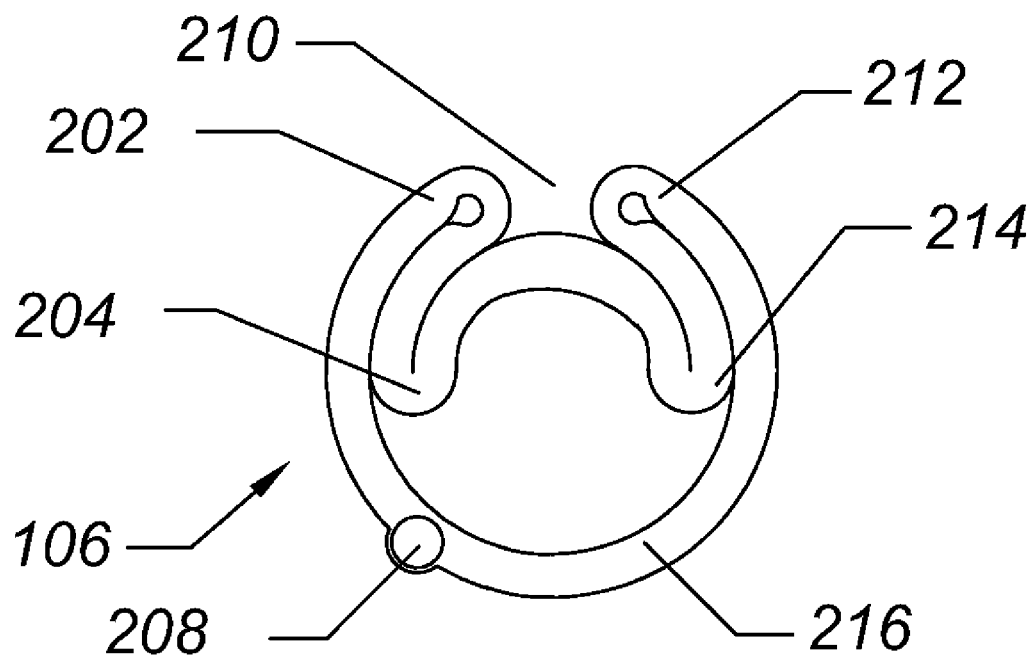
FIG. 2B illustrates a lateral cross-section of the distal expandable section of a sheath comprising two folds, according to one embodiment.

FIG. 2B illustrates a lateral cross-sectional view of one embodiment of a folded distal section 106 comprising a distal section wall 216. The distal section wall 216 may comprise a double fold 210 further comprising two outside edges 202 and two inside edges 212. When the diameter of the sheath increases, it becomes advantageous to form a plurality of folds in the wall 216. For a sheath having a fully expanded outside diameter ranging between 12 French and 30 French and with a wall thickness ranging between 1 and 2-French, a double fold 210, as illustrated in FIG. 2B is preferred. A double fold 210, for example can allow a 14 French outside diameter sheath to fold into a collapsed diameter of around 9 to 12 French. An 18-French outside diameter sheath having a 1 to 2-French wall thickness can be folded into a collapsed diameter of around 12 to 13 French using a double fold. The sheath wall 216 may further comprise an optional balloon inflation lumen 208 for use in transmitting fluidic pressure or energy from the sheath hub to distal regions of the sheath wherein a balloon can be affixed. The diameter of the balloon inflation lumen 208 can range between 0.005 to 0.025 inches.

It should be appreciated in the embodiments described above that the longitudinal folds 208, 210 of FIGS. 2A and 2B, respectively, or modifications thereof can be used to provide an expandable region of the catheter (described above) with an initial small cross-sectional diameter. By unfolding the distal region 106, the diameter of the distal region 106 can be increased to a larger diameter. In the smaller folded configuration, the malleable structures described above can maintain the distal region 106 in the smaller folded configuration. In other embodiments, an external structure can maintain the sheath in the folded configuration. In this smaller folder configuration it has been noted that the flexibility of the catheter (e.g., the ability of the catheter to navigate the aortic arch) is increased. When the catheter is unfolded and expanded, the malleable structure can reform to the larger unfolded diameter and to the shape of the anatomy in which the sheath his placed. In the unfolded configuration, the malleable structures provide hoop strength to maintain the patency of the lumen.

Figure 3:
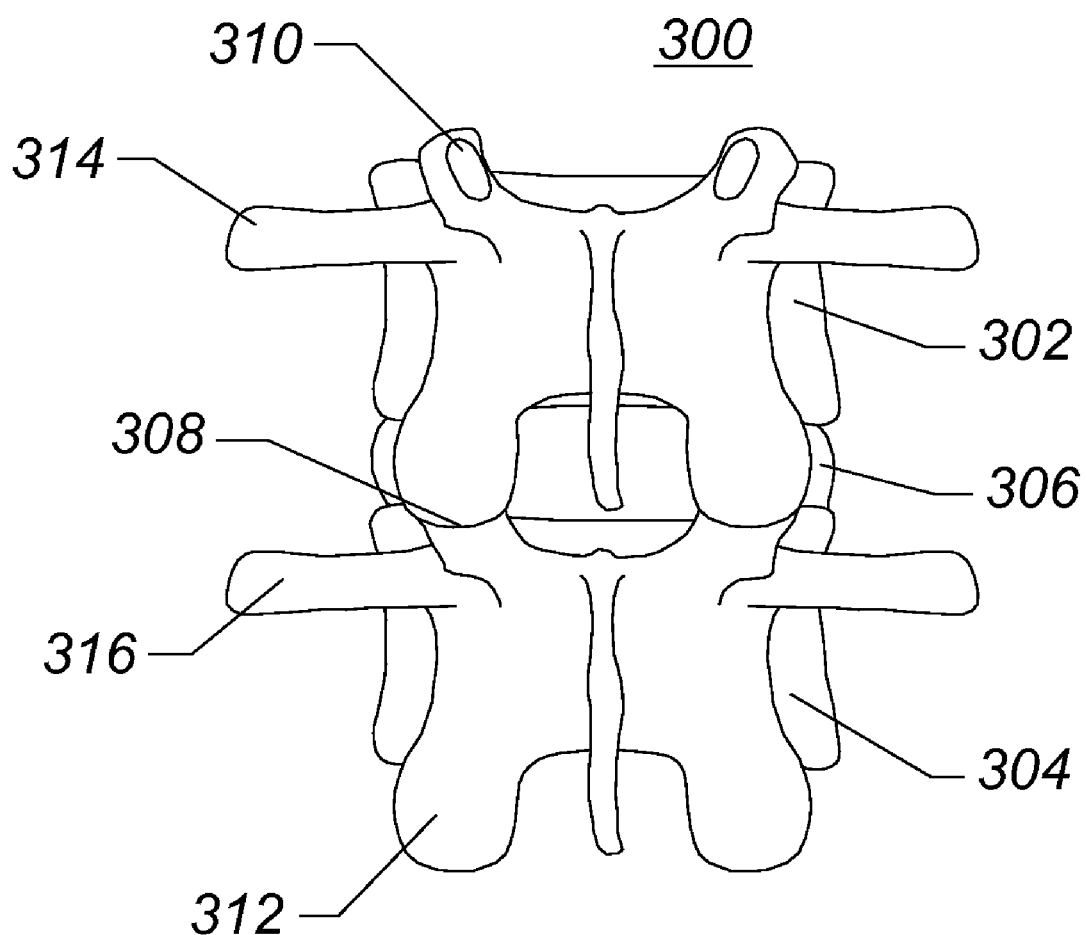
FIG. 3 illustrates a posterior view of a lumbar vertebral motion segment.

FIG. 3 illustrates a spinal motion segment 300, as viewed from the posterior direction, comprising an upper vertebra 302, a lower vertebra 304, an intervertebral disc 306, a plurality of facet joints 308, a plurality of superior facets 312, a plurality of inferior facets 310, and a plurality of pedicles 314 and 316.

Referring to FIG. 3, damage or wear often occurs to the intervertebral disc 306. The intervertebral disc 306 comprises an annulus, made up of tough, fibrous, soft tissue oriented in a circumferential direction. The intervertebral disc also comprises a central region, called the nucleus, which is gel-like and comprises polymucosaccharides. The intervertebral disc separates the upper vertebra 302 from the lower vertebra 304. The vertebra 302 and 304 comprise an exterior of hard, cortical bone with a core of softer cancellous bone. Projections from the posterior aspect of the vertebra 302, 304 meet and form joints called facet joints 308 which are sliding joints for spinal motion. Access to the intervertebral disc 306 is hindered from a posterior approach by the presence of the pedicles 314, 316, the facets, 310, 312, the spinal cord (not shown) and the nerve roots (not shown) that are routed through the openings within the structure of the motion segment 300.

Figure 4:
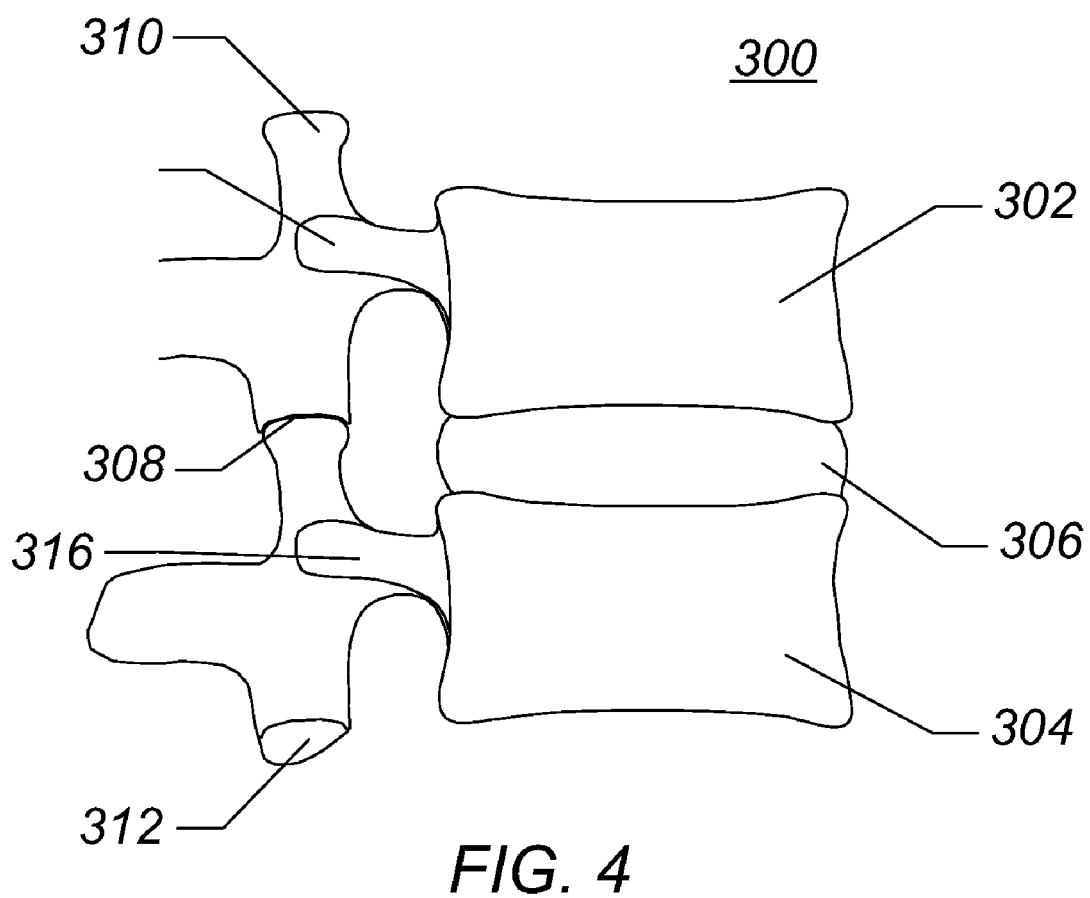
FIG. 4 is a side view of a lumbar vertebral motion segment.

FIG. 4 illustrates the spinal motion segment 300 from the right lateral direction. The motion segment comprises the upper vertebra 302, a lower vertebra 304, an intervertebral disc 306, a plurality of facet joints 308, a plurality of superior facets 312, a plurality of inferior facets 310, and a plurality of pedicles 314 and 316.

From the lateral direction, access to the intervertebral disc 306 is improved as many of the bony structures and nerve roots are disposed posteriorly and do not interfere with this lateral approach. Such access is similar for both the right and left lateral approaches.

Figure 5:
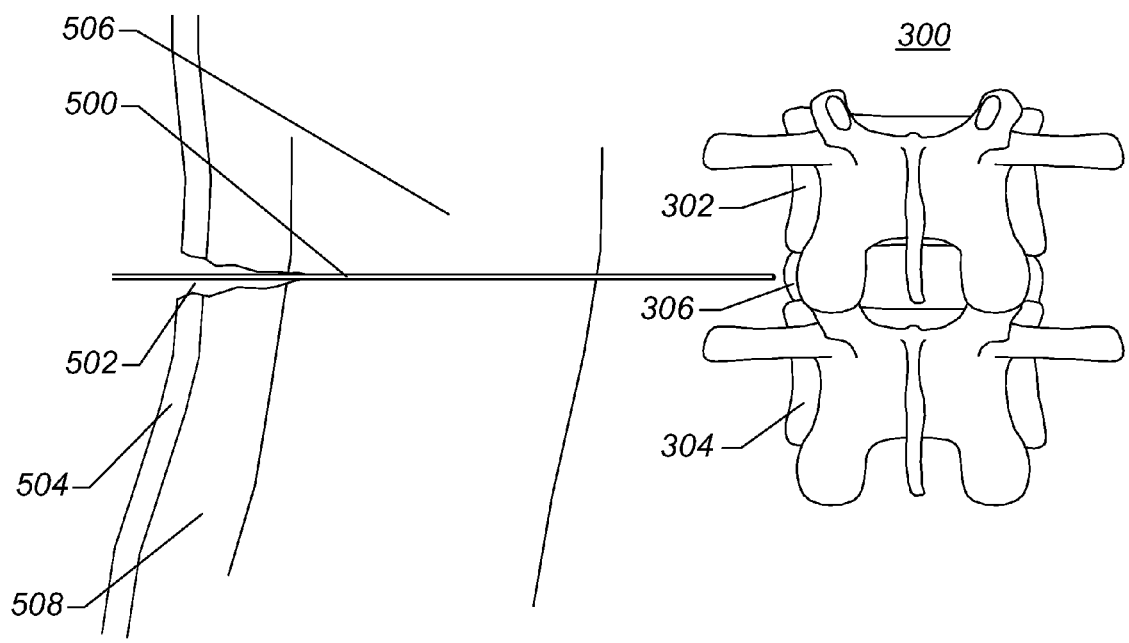
FIG. 5 illustrates a guidewire advanced through a skin incision, through the Psoras muscle and routed laterally to a lumbar intervertebral disc, according to one embodiment.

FIG. 5 illustrates a posterior view of a lumbar spine motion segment 300 comprising the upper vertebra 302, the intervertebral disc 306, and the lower vertebra 304. A guidewire 500 is shown being advanced toward the intervertebral disc 306 by way of an incision 502 in the skin 504. The incision also passes through fat layers 508 and muscle layers 506 on its path to the intervertebral disc. The approach is being made from the left lateral direction. The large muscle 508 illustrated is the Psoras muscle, which is highly innervated. The guidewire 500 is generally a very stiff wire with a diameter of about 0.035 to 0.038 inches.

Figure 6:
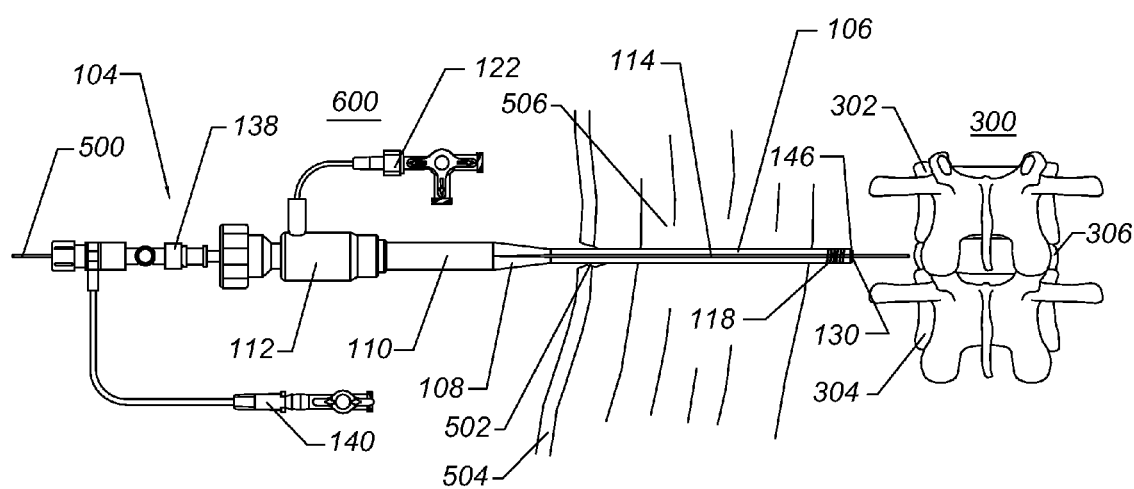
FIG. 6 illustrates an expandable spinal access sheath advanced over the guidewire such that its distal end approaches the lumbar spine, according to one embodiment.

FIG. 6 illustrates one embodiment of an expandable spinal sheath 600 being advanced through the incision 502 through the skin 504 and along the guidewire 500 with its distal end approaching the intervertebral disc 306. The sheath system 600 passes through the Psoras muscle 506 with less risk of injuring vasculature or nerves than would a larger diameter sheath. The collapsed, expandable sheath system 600 may comprise the sheath hub 112, the proximal non-expandable region 110, the transition zone 108, the distal expandable region 106, further comprising the longitudinal fold 114, the sheath purge port 122, and the radiopaque marker 118. The dilator 104, within the sheath system 600, may comprise the dilator hub 138, the dilator balloon 146, and the central dilator tubing 130.

Referring to FIG. 6, advancement of the sheath 600 with the radially collapsed distal end 106 requires less force than advancing larger sheaths and is more capable of following a guidewire path than would a larger diameter sheath. In other embodiments, the sheath dilator 104 can comprise a tapered fairing or nose cone (not shown) at its distal end to facilitate advancement through the tissue tract. In this embodiment, the balloon 146 is affixed to the central dilator shaft 130 with an inverted bond to minimize projection of the dilator out the distal end of the sheath expandable region 106.

To initiate the procedure, following a standard sterile preparation, a hollow needle may be inserted percutaneously and advanced into the skin 504 with the aid of fluoroscopy. The hollow needle can be 16 or 18 gauge. The hollow needle preferably comprises a Tuohy-Borst fitting at its proximal end for fluid control.

Thus the expandable percutaneous spinal access sheath 600 or 100 is inserted to create a portal to access and treat spinal pathologies. The establishment of this channel or portals facilitates the passage of other deployment catheters or instruments carrying orthopedic reamers, sizers, implantation delivery systems, implants, and the like. An example of such a deployment catheter with an inflatable orthopedic fixation device at its distal end as well as the associated anchors and methods are disclosed in U.S. patent application Ser. No. 10/161,554 filed on May 31, 2002, the disclosure of which is hereby incorporated by reference in its entirety.

Figure 7:
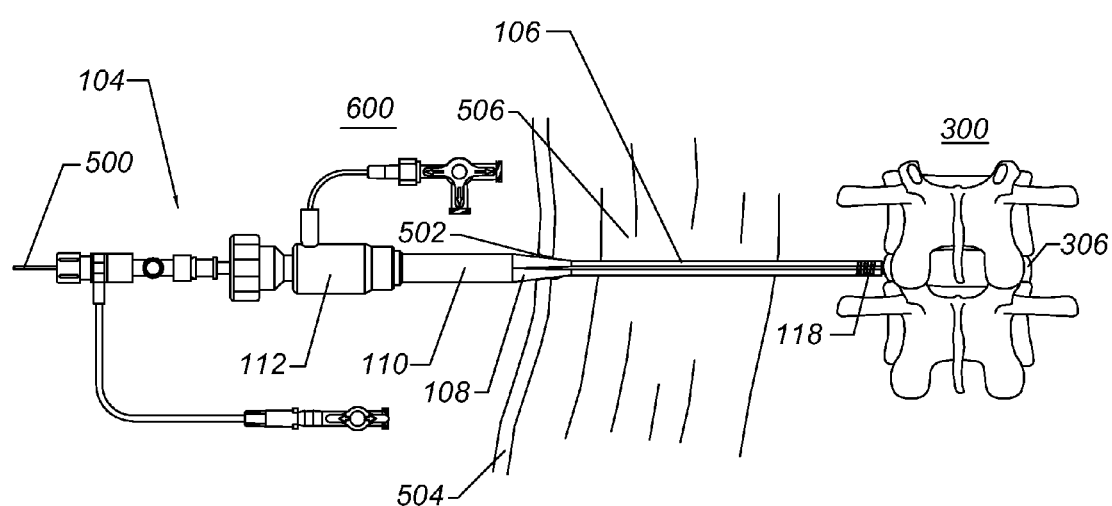
FIG. 7 illustrates the diametrically collapsed spinal access sheath advanced over the guidewire such that its distal end resides proximate the lumbar spine, according to one embodiment.

FIG. 7 illustrates an embodiment of the spinal sheath 600 being fully advanced along the guidewire 500 with its distal end proximate the intervertebral disc 306. The radiopaque marker 118 is visible under fluoroscopy and can be used to confirm correct sheath positioning at this point in the procedure. The expandable region remains unexpanded as the dilator 104 has not yet been inflated.

Figure 8:
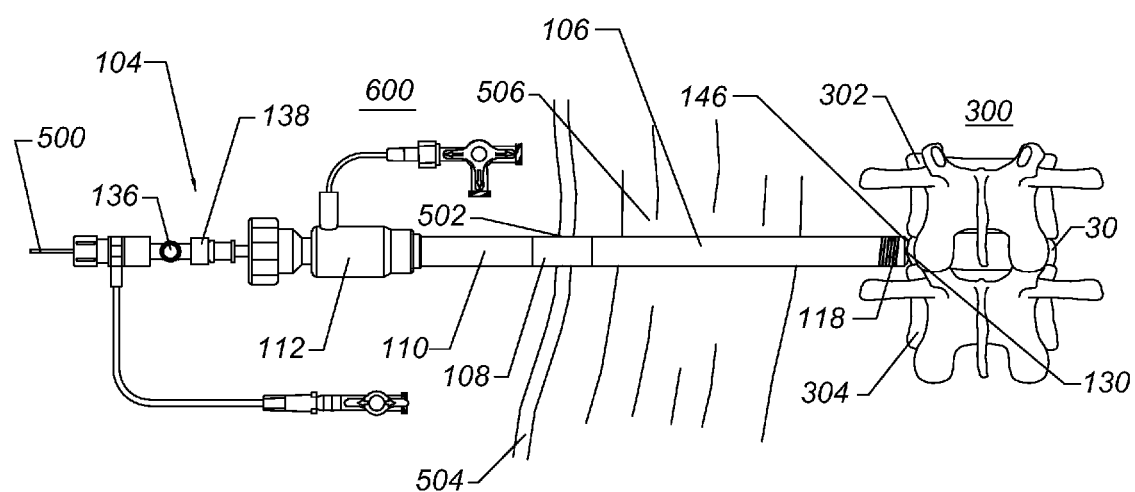
FIG. 8 illustrates the expandable spinal access sheath residing proximate the intervertebral disc and with its expandable portion dilated to its full operating cross-section, according to one embodiment.

FIG. 8 illustrates an embodiment of the spinal sheath 600 with the balloon 146 of the dilator 104 having been expanded using incompressible liquid injected through the balloon inflation port 136 in the dilator hub 138. The guidewire 500 remains in place. The distal expandable region 106 is fully expanded, as is the transition zone 108. The transition zone 108 is generally located about the level of the skin 504. The proximal region 110 is now about the same size as the distal region 106. The radiopaque marker 118 has expanded along with the distal region 106 since it can unfold. The balloon 146 with the inverted bond to the sheath tubing 130 allows close proximity between the sheath distal end and the intervertebral disc 306. The Psoras muscle 506, and other adjacent muscles such as the lumbar muscles, are now fully dilated with a minimally invasive procedure.

Figure 9:
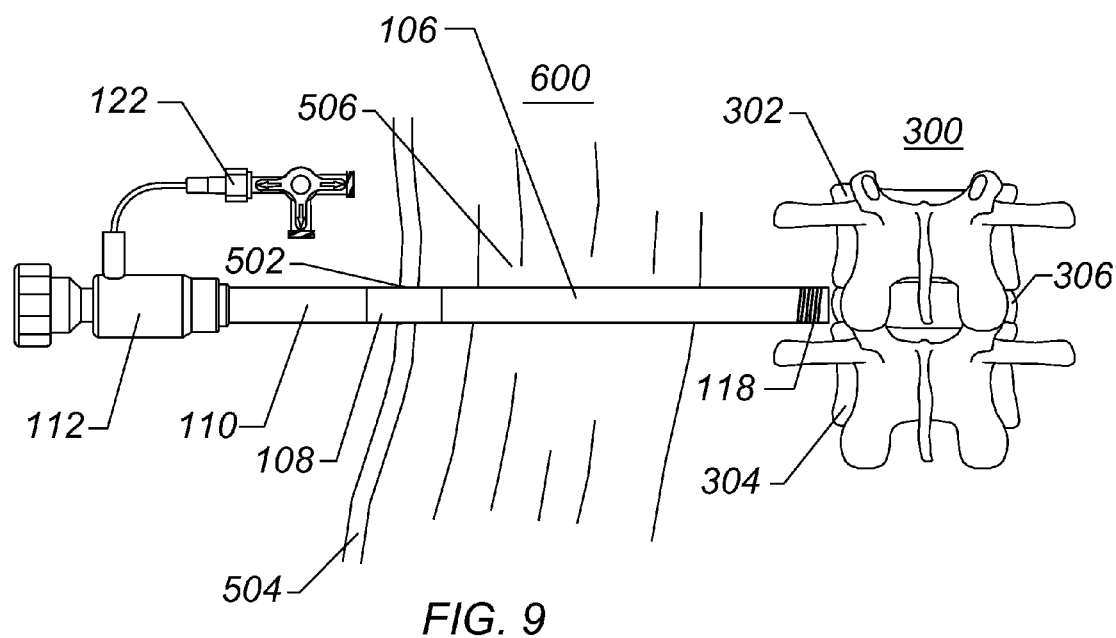
FIG. 9 illustrates the expanded sheath following removal of the dilator, according to one embodiment.

FIG. 9 illustrates an embodiment of the fully, diametrically, expanded sheath 600 with its dilator 104 and the guidewire 500 (FIG. 8) having been removed. The central lumen of the sheath 600 is now available for instrument passage toward the intervertebral disc 306, situated between the inferior vertebra 304 and the superior vertebra 302. Flushing of the lumen can be accomplished with the purge line 122 affixed to the sheath hub 112.

Figure 10:
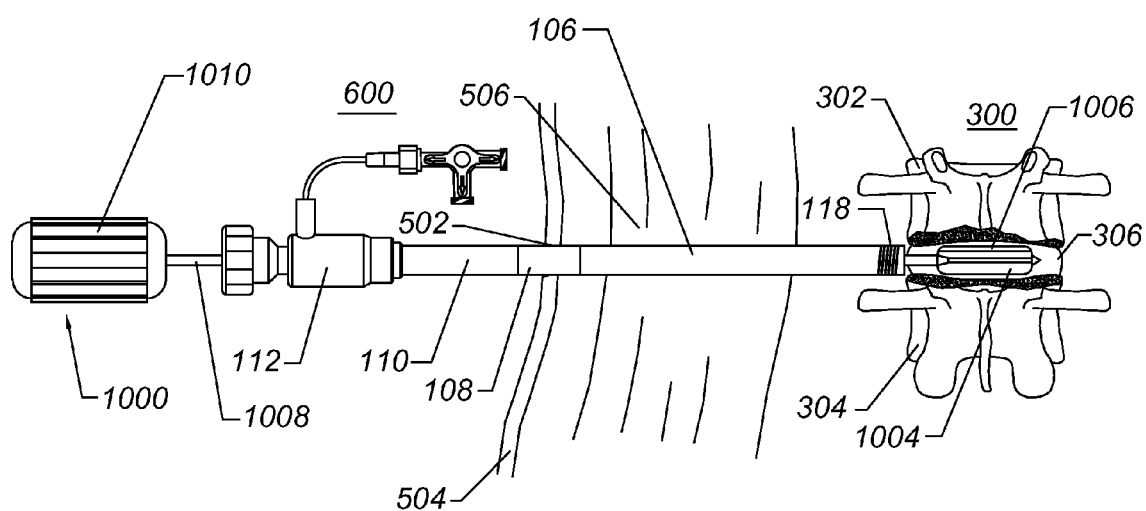
FIG. 10 illustrates introduction of a preparation instrument through the sheath for the purpose of removing intervertebral disc material, according to one embodiment.

FIG. 10 illustrates a side view of an embodiment of the expandable spinal sheath 600 being used for the XLIF procedure. The intervertebral disc 306, the upper vertebra 302, and the lower vertebra 304 are illustrated in partial breakaway view. A rotary tissue removal tool or reamer 1000 has been inserted through the sheath hub 112, through the proximal sheath tube 110, the transition zone 108, and the expandable distal region 106 and into the intervertebral disc 306. The reamer 1000 comprises a handle 1010, a shaft 1008, and a reamer bit 1004 further comprising a plurality of cutting edges 1006. The reamer 1000 preferably comprises two cutting edges 1006 but the number of cutting edges can range between 1 and 8. The reamer 1000 preferably comprises deep flutes to allow tissue to collect therein for removal from the patient. The reamer 1000 can be rotated about its axis by an operator such that the cutting edges 1006 rotate about the central longitudinal axis of the reamer 1000. The reamer bit 1004 may be configured to pass through the expanded sheath tubing lumen. The reamer 1000 is being used to remove nucleus tissue as well as annulus tissue but is not being used to remove bone in this example. The shaft 1008 can seal on the hub 112 or the hub 112 can remain open so that visualization instrumentation can be passed therethrough to observe the procedure.

Figure 11:
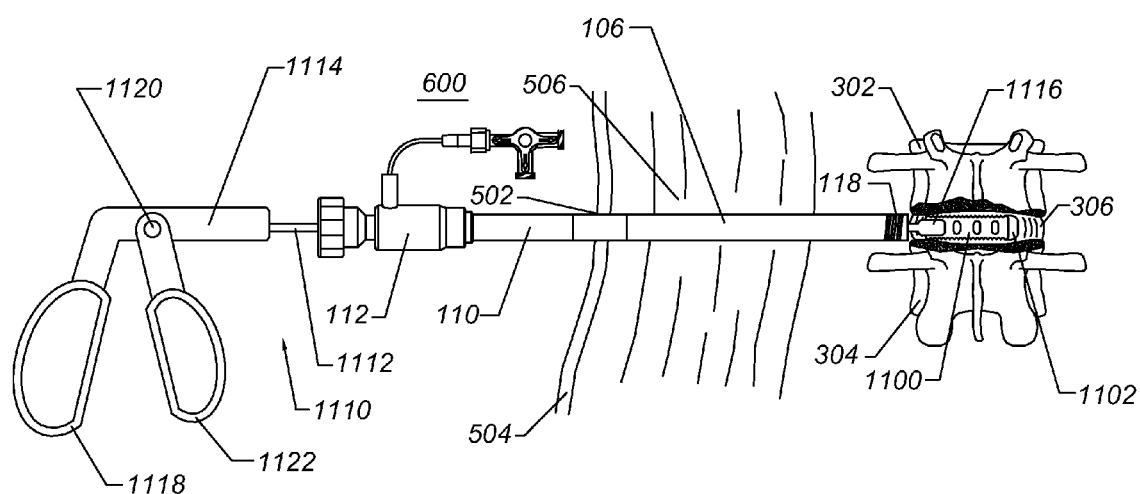
FIG. 11 illustrates introduction of a vertebral inner body fusion device, according to one embodiment.

FIG. 11 illustrates the next step in the procedure. The reamer 1000 has been removed and an implant 1100 is being placed through the expandable spinal sheath 600 using a delivery system 1114. The implant 1100 is being placed in the void 1102 created by the reamer 1000. The implant 1100 is releasably held by the graspers 1116, which are affixed to the distal end of the delivery system 1110. The graspers 1116 are operably connected to the trigger 1122, which is rotatably connected to the delivery system 1110 by the hinge 1120. The delivery system 1110 also comprises a rear handle portion 1118, against which the trigger 1116 can be pulled to activate the graspers 1116. The graspers 1116 are connected to the trigger 1122 by means of a linkage, slidably, or rotatably, disposed along the length of the delivery system 1110. Again, a fiberoptic telescope (not shown) with light source can be advanced through the sheath 600 along with the delivery system to view the implantation.

Figure 12:
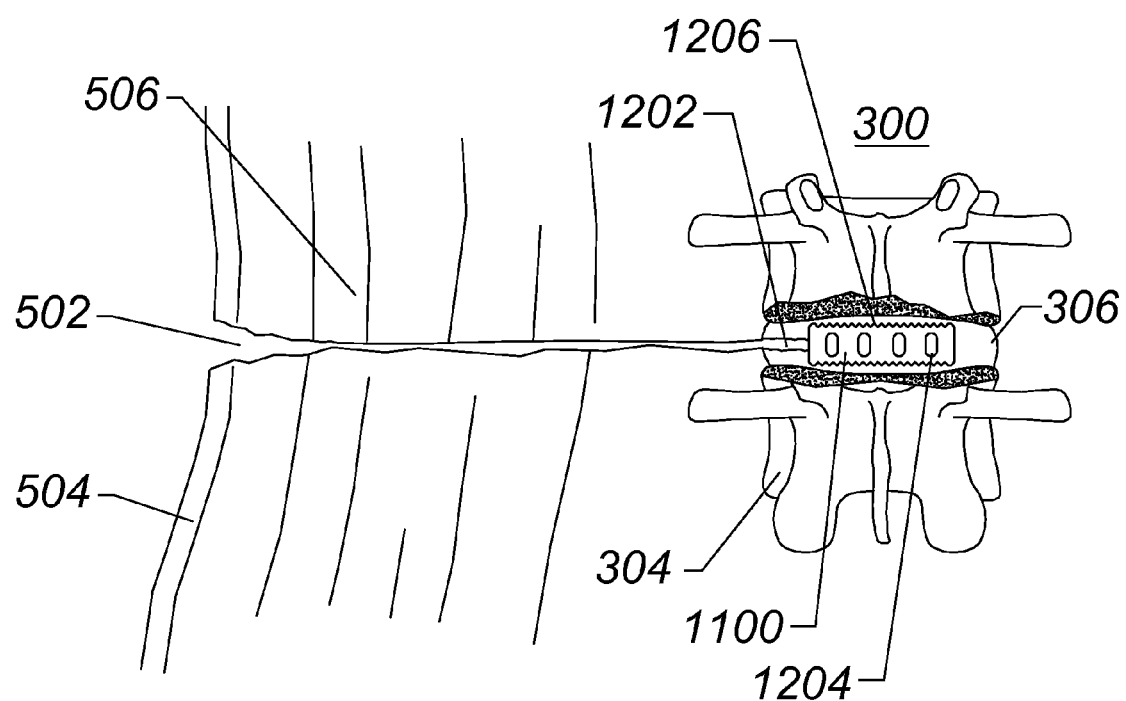
FIG. 12 illustrates removal of the sheath leaving the inner body fusion device, according to one embodiment.

FIG. 12 illustrates the implant 1100 centered within the intervertebral disc 306. The spinal sheath 600 has been removed along with the delivery system 1110. The tissue tract 1202 remains leading from the skin incision 502 to the defect remaining in the annulus of the intervertebral disc 306. The implant 1100 comprises perforations 1204 to enhance tissue ingrowth as well as serrations 1206 to enhance ultimate mating with the cortical bone of the vertebrae 302, 304. The implant 1100 can be fabricated from PEEK, titanium, or similar biocompatible materials of polymeric or metallic origin. Closure of the incision 502 in the skin 504 can be accomplished using sutures, clips, or the like. Closure of muscle tissue 506 can be similarly accomplished. Closure of the defect in the annulus of the intervertebral disc 306 can be accomplished with a plug device, mesh, or other closure system.

Figure 13A:
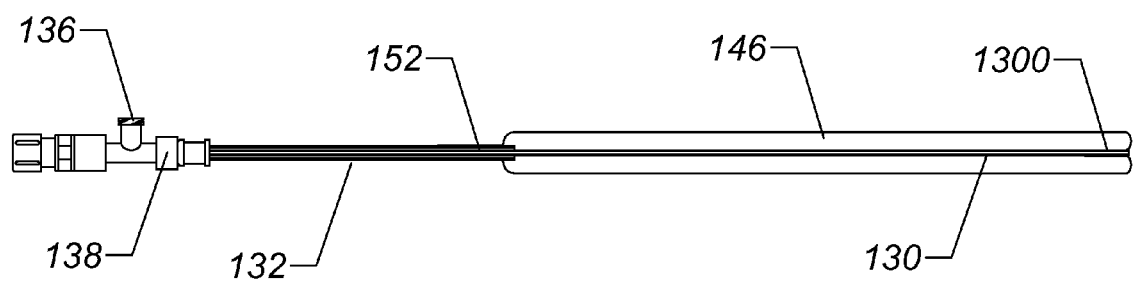
FIG. 13A illustrates a side view of a dilator comprising a dilator balloon affixed at its distal end to the dilator tubing with an inverted bond, according to one embodiment.

FIG. 13A illustrates an embodiment of a dilator comprising a balloon 146 further comprising an inverted distal bond 1300 that affixes the balloon 146 to the inner tubing 130. The proximal bond 152 may be a standard external bond that affixes the balloon to the outer dilator tubing 132. Inflation of the balloon 146 may occur through the balloon inflation port 136 affixed or integral to the dilator hub 138. To create the inverted bond 1300 the bond 1300 may be generated first with the balloon 146 uninverted and projecting distally. The balloon 146 may next be pulled proximally by rolling. The larger diameter of the proximal bond 152 permits inversion of the balloon and proximal disposition. Following positioning of the proximal bond 152 over the proximal tubing 132, the proximal bond is completed. The bonds 152, 1300 can be created using heat and pressure or polyurethane based ultraviolet light curing adhesives, or both. The balloon 146 can be fabricated from PET or other high strength material that can be stretch blow molded to orient the long chain molecules for maximum strength.

Figure 13B:
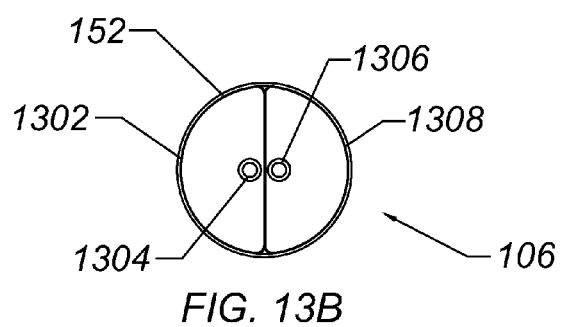
FIG. 13B illustrates a lateral cross-sectional view of a spinal access sheath with its distal region expanded, wherein the dilator comprises a plurality of expandable balloons, according to one embodiment.

FIG. 13B illustrates a lateral cross-sectional view of an embodiment of the expandable distal region 106 of a sheath wherein two balloons 1302, 1308 are disposed asymmetrically around two dilator tubes 1304, 1306. The sheath outer wall 152 is fully dilated by the two balloons 1302, 1308. Inflation of only one balloon can partially dilate the outer wall 152 allowing for expansion to an intermediate diameter prior to full expansion. Each balloon 1302, 1308 may be separately inflated through separate inflation ports at the proximal end of the dilators.

One method of using the percutaneous access sheath 100 to facilitate the insertion of an orthopedic spinal stabilization implants formed in situ according to one aspect of the present invention is described in the accompanying figures. While the method is disclosed and depicted with reference to only two vertebrae, one of which is either unstable, separated or displaced and the other of which is neither unstable, separated or displaced, the method can also be applied to three or more vertebrae simultaneously. Further, the method can be used to stabilize or separate the L5 vertebrae 304 from the L4 vertebra 302. Although the method is disclosed and depicted as applied on the left side of the vertebral column, the method can also be applied on the right side of the vertebral column or, preferably, on both sides of the vertebral column, as will be understood by those skilled in the art with reference to this disclosure. Other applications include the stabilization of other bones and skeletal elements of the body.

It should be noted that the sheath hub 112 can be affixed to a stabilizer instrument further clamped to the patient, to the bed, or to another fixture in the operating theatre. The stabilizer instrument can be releasably affixed to the hub 112 by a clamp, clip, fastener, or the like.

Figure 14A:
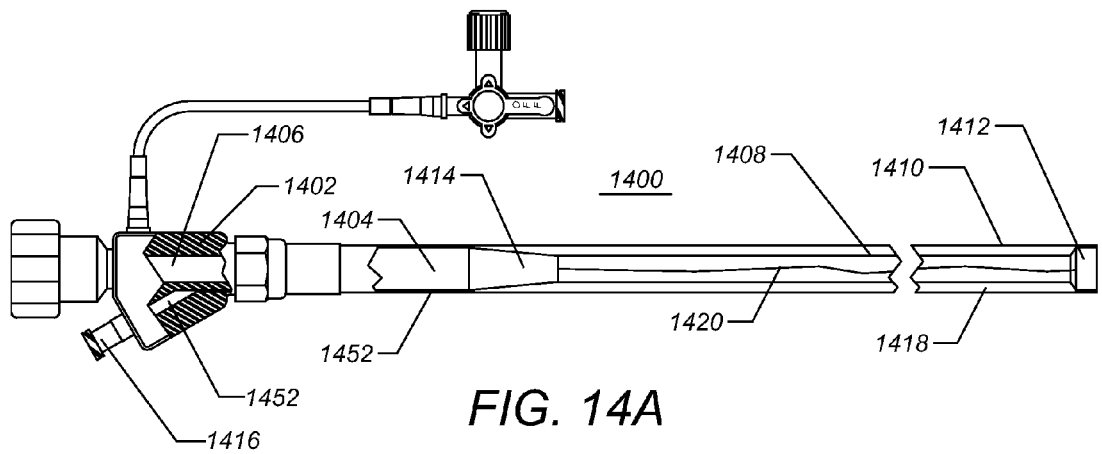
FIG. 14A illustrates a lateral view of a spinal access sheath following re-collapse of a the distal expandable sheath tubing due to pressurization in the space between the distal sheath tubing and a still expanded outer pressure jacket, according to one embodiment.

FIG. 14A illustrates a side view of an embodiment of a re-collapsible sheath 1400, in partial breakaway view, for introducing a spinal instrument, wherein the sheath 1400 comprises a hub 1402 further comprising a refolding inflation port 1416, a refolding lumen 1452, and a central lumen 1406. The sheath 1400 may further comprise a length of proximal, non-expandable sheath tubing 1404 further comprising the re-collapse lumen 1452, a distal expandable sheath region 1408 further comprising a longitudinal fold 1420, a pressure jacket 1410, a distal pressure jacket bond 1412, a re-collapse volume 1418, and a transition zone 1414. The sheath 1400 is shown with its distal collapsible region 1408 in its collapsed state with the pressure jacket 1410 still inflated.

Referring to FIG. 14A, the dilator has been removed leaving behind the open sheath lumen 1406. The distal pressure jacket bond 1412 is preferably a heat weld between the pressure jacket 1410 and the distal sheath tubing 1408. The length of the bond 1412 can range from about 0.01 inches to 0.25 inches. The bond 1412 can be generated using shrink tubing, a mandrel, and a hot box. The bond 1412 can also be generated using a laser balloon bonding system. A lathe or turntable is a beneficial addition to the tooling to ensure correct application of heat in a distributed fashion to create the bond. The distal sheath tubing 1408 can be fabricated using a sandwich of Hytrel tubing with the malleable stainless steel reinforcing coil embedded therein. Radiopaque markers and reinforcing polymeric bands, fabricated from, for example, PET, can be embedded within the Hytrel or other polymer tube. The wall thickness of the distal sheath tubing 1408 can range from about 0.005 to about 0.020 inches. The proximal end of the pressure jacket 1410 may be affixed, welded, bonded, or connected, both physically and sealingly, to the proximal sheath tubing 1404 or to parts of the hub 1402. The pressure jacket 1410 may be substantially non-elastomeric or malleable and limited in its ability to expand. Thus, increasing the pressure within the gap 1418 does not substantially increase the diameter of the pressure jacket 1410 but it does cause the inner material 1408 to be crushed or collapse inward.

Figure 14B:
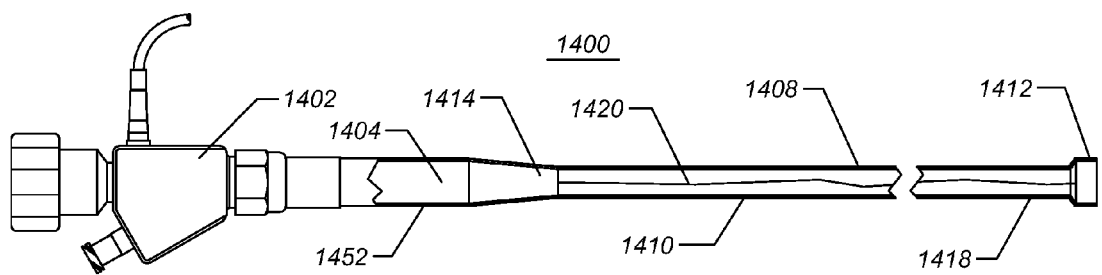
FIG. 14B illustrates a lateral view of the collapsed spinal access sheath of FIG. 14A, following evacuation of fluid between the inner layers of the distal expandable sheath tubing and the outer pressure jacket and subsequent re-collapse of the outer pressure jacket, according to one embodiment.

FIG. 14b illustrates a side view of an embodiment of a sheath 1400 in partial breakaway view. The sheath 1400 comprises the hub 1402, the proximal non-expandable sheath region 1404 further comprising the refolding pressurization lumen 1452. The sheath 1400 may also comprise a length of expandable sheath distal tubing 1408 further comprising a fold line 1420, a pressure jacket 1410, the distal pressure jacket bond 1412, and the re-collapse volume 1418 between the sheath tubing 1408 and the pressure jacket 1410. The sheath 1400 is illustrated following removal of the dilator (not shown). The dilator (not shown) may be as described elsewhere in this document.

Referring to FIG. 14B, the pressure within the gap between the distal sheath tubing 1408 and the pressure jacket 1410 has been evacuated, which results in the flexible pressure jacket 1410 being drawn inward against the distal sheath tubing 1408, which was collapsed on the prior step. The sheath 1400 is now ready to be removed from the patient with minimal resistance. The distal bond 1412 between the jacket 1410 and the tubing 1408 may not collapse completely but some collapse will occur and the system will still retain a smaller removal force than will a fully expanded sheath.

It also should be noted that certain objects and advantages of the inventions have been described above for the purpose of describing the inventions and the advantages achieved over the prior art. Of course, it is to be understood that not necessarily all such objects or advantages may be achieved in accordance with any particular embodiment of the inventions. Thus, for example, those skilled in the art will recognize that the inventions may be embodied or carried out in a manner that achieves or optimizes one advantage or group of advantages as taught herein without necessarily achieving other objects or advantages as may be taught or suggested herein.

Moreover, although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of these inventions, will be readily apparent to those of skill in the art based upon this disclosure. For example, it is contemplated that various combination or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

What is claimed is:

1. A method of introducing instruments or implants into a target region proximate the human spinal column, the method comprising the steps of:
   creating a skin incision at a lateral position on a patient near a level of a spinal region to be treated;
   inserting a guidewire into the skin incision and routing the guidewire to a target region of the spine through a muscle, the muscle comprising one of a Psoras muscle and lumbar muscle;
   inserting a collapsed sheath, with a dilator pre-inserted and an outer pressure jacket, over the guidewire such that the distal end of the collapsed sheath is proximate the target region of the spine;
   radially expanding an expandable region of the sheath with the dilator, to create an expanded sheath, so that the expandable region radially dilates the muscle and forms a channel through the muscle;
   removing the dilator from a remaining lumen of the expanded sheath;
   performing therapy or diagnosis at the target region through the lumen of the expanded sheath;
   pressurizing a space between the outer pressure jacket and expandable region to collapse the expandable region;
   evacuating the space between the outer pressure jacket and collapsed expandable region to draw the outer pressure jacket inward; and
   removing the sheath from the patient.

2. The method of claim 1, further comprising the step of affixing a hub to a stabilizer positioned outside the patient, wherein the hub is affixed to the proximal end of the sheath.

3. The method of claim 1, further comprising inserting therapeutic or diagnostic instruments through the expanded sheath.

4. The method of claim 1, further comprising inserting or removing spinal implants through the expanded sheath.

5. The method of claim 1, wherein the therapy comprises removing spinal material through the expandable sheath.

6. The method of claim 1, wherein the step of expanding the dilator causes radial dilation of the muscle and adjacent tissue.

7. The method of claim 1, wherein the therapy comprises placement of a vertebral body spacer between the vertebrae.

8. The method of claim 1, wherein the therapy comprises placement of an annular repair device between the vertebrae.

9. The method of claim 1, wherein the expansion of the distal region comprises a first expansion step from the first, unexpanded configuration to a second, intermediate configuration followed by a second expansion step from the second, intermediate configuration to the final fully expanded configuration.

10. The method of claim 1, wherein the dilation of the distal region step comprises advancing a hollow, axially elongate dilator distally through the collapsed distal expandable region.

11. A method of introducing instruments or implants into a target region proximate the human spinal column, the method comprising the steps of:
   creating a skin incision on a patient near a level of a spinal region to be treated;
   inserting a guidewire into the skin incision and routing the guidewire to a target region of the spine through a muscle, the muscle comprising one of a Psoras muscle and lumbar muscle;
   inserting a sheath, comprising an expandable region in a collapsed configuration with a pre-inserted dilator, over the guidewire such that the distal end of the sheath is proximate the target region of the spine, the expandable region comprising a malleable reinforcement embedded between outer and inner polymeric layers and, in the collapsed configuration, a double fold, the double fold comprising two longitudinal outside edges and two longitudinal inside edges;
   radially expanding the expandable region of the sheath with the dilator to an expanded configuration, so that the expandable region radially dilates the muscle and forms a channel through the muscle;
   removing the dilator from a remaining lumen of the expandable region;
   performing therapy or diagnosis at the target region through the lumen of expandable region; and
   removing the sheath from the patient;

wherein the malleable reinforcement is configured to maintain the expandable region in the collapsed configuration and, when the expandable region is expanded, reform to provide hoop strength to the expandable region in the expanded configuration.

12. The method of claim 11, further comprising the step of affixing a hub to a stabilizer positioned outside the patient, wherein the hub is affixed to the proximal end of the sheath.

13. The method of claim 11, further comprising inserting therapeutic or diagnostic instruments through the expandable region.

14. The method of claim 11, further comprising inserting or removing spinal implants through the expandable region.

15. The method of claim 11, wherein the therapy comprises removing spinal material through the expandable region.

16. The method of claim 11, wherein the step of expanding the expandable region causes radial dilation of the muscle and adjacent tissue.

17. The method of claim 11, wherein the therapy comprises placement of a vertebral body spacer between the vertebrae.

18. The method of claim 11, wherein the therapy comprises placement of an annular repair device between the vertebrae.

19. The method of claim 11, wherein expansion of the expandable region comprise a first expansion step from the collapsed configuration to an intermediate configuration followed by a second expansion step from the intermediate configuration to the expanded configuration.

20. The method of claim 11, wherein the dilation of the expandable region step comprises advancing a hollow, axially elongate dilator distally through the expandable region.

21. The method of claim 20, further comprising the step of re-collapsing the expandable region of the sheath to a smaller diameter prior to removing the sheath from the patient.

* * * * *